US008748385B2

(12) United States Patent
O'Shea et al.

(10) Patent No.: US 8,748,385 B2
(45) Date of Patent: Jun. 10, 2014

(54) ADULT CEREBELLUM-DERIVED NEURAL STEM CELLS AND COMPOSITIONS AND METHODS FOR PRODUCING OLIGODENDROCYTES

(75) Inventors: Kathy Sue O'Shea, Ann Arbor, MI (US); Maria Morell, Granada (ES)

(73) Assignee: Regents of the University of Michigan, Ann Arbor, MI (US)

( * ) Notice: Subject to any disclaimer, the term of this patent is extended or adjusted under 35 U.S.C. 154(b) by 33 days.

(21) Appl. No.: 13/375,269

(22) PCT Filed: Jun. 8, 2010

(86) PCT No.: PCT/US2010/037789
§ 371 (c)(1),
(2), (4) Date: Apr. 23, 2012

(87) PCT Pub. No.: WO2010/147803
PCT Pub. Date: Dec. 23, 2010

(65) Prior Publication Data
US 2012/0202745 A1 Aug. 9, 2012

Related U.S. Application Data

(60) Provisional application No. 61/184,972, filed on Jun. 8, 2009, provisional application No. 61/185,088, filed on Jun. 8, 2009.

(51) Int. Cl.
*A61K 38/17* (2006.01)
*C12N 5/079* (2010.01)

(52) U.S. Cl.
USPC .......................................... 514/17.7; 435/377

(58) Field of Classification Search
None
See application file for complete search history.

(56) References Cited

U.S. PATENT DOCUMENTS 4,736,866 A 4/1988 Leder et al.
4,873,191 A 10/1989 Wagner et al.
5,843,775 A * 12/1998 Valenzuela et al. ............ 435/325

FOREIGN PATENT DOCUMENTS

WO   WO 02/26941    4/2002
WO   WO 2008/068589  6/2008

OTHER PUBLICATIONS

Izrael et al., Human oligodendrocytes derived from embryonic stem cells: Effect of noggin on phenotypic differentiation in vitro and on myelination in vivo, Mar. 2007, Mol. Cell. Neurosci. 34(3):310-323.*
GenBank Accession No. AAA51699, Oct. 31, 1994, 1 page.
GenBank Accession No. AAB38281, Dec. 9, 1996, 1 page.
GenBank Accession No. AAC05174, Dec. 21, 1999, 1 page.
GenBank Accession No. 0005US1, Jul. 15, 2006, 2 pages.
GenBank Accession No. AAH34027, Jul. 15, 2006, 2 pages.
GenBank Accession No. AAH93733, Jul. 17, 2006, 2 pages.
GenBank Accession No. AF065917, Jun. 1, 1998, 1 page.
GenBank Accession No. BAA19511, Dec. 27, 2006, 1 page.
GenBank Accession No. BAA31357, Jul. 9, 1998, 1 page.
GenBank Accession No. BC069540, Jul. 15, 2006, 2 pages.
GenBank Accession No. BC093733, Jul. 17, 2006, 2 pages.
GenBank Accession No. BC169672, Nov. 20, 2008, 2 pages.
GenBank Accession No. CAA00190, Mar. 1, 1993, 1 page.
GenBank Accession No. CAI25201, Jan. 15, 2009, 2 pages.
GenBank Accession No. EAW94528, Feb. 4, 2010, 2 pages.
GenBank Accession No. EDM00223, Jun. 20, 2007, 1 page.
GenBank Accession No. NM_002309, Jun. 1, 1998, 1 page.
GenBank Accession No. NM_005450, Mar. 26, 2012, 4 pages.
GenBank Accession No. NM_008501, Mar. 24, 2012, 4 pages.
GenBank Accession No. NM_008711, Mar. 17, 2012, 3 pages.
GenBank Accession No. NM_008711.2, Mar. 17, 2013, 3 pages.
GenBank Accession No. NM_012990, Nov. 11, 2011, 3 pages.
GenBank Accession No. NM_022196, Mar. 3, 20120, 3 pages.
GenBank Accession No. NM_031048, Nov. 19, 2011, 4 pages.
GenBank Accession No. NM_214402, Feb. 12, 2012, 2 pages.
GenBank Accession No. NP_001079113, Mar. 10, 2012, 2 pages.
GenBank Accession No. NP_001137163, Nov. 14, 2011, 1 page.
GenBank Accession No. NP_002300, Apr. 1, 2012, 3 pages.
GenBank Accession No. NP_005441, Mar. 26, 2012, 3 pages.
GenBank Accession No. NP_032737, Mar. 17, 2012, 2 pages.
GenBank Accession No. NP_037122, Nov. 11, 2011, 2 pages.
GenBank Accession No. NP_989454, Mar. 11, 2012, 2 pages.
GenBank Accession No. NP_999567, Feb. 12, 2012, 2 pages.
GenBank Accession No. U65394, Dec. 25, 1996, 2 pages.
GenBank Accession No. X06381.1, Jul. 13, 1995, 2 pages.
Arlotta et al., "Ctip2 Controls the Differentiation of Medium Spiny Neurons and the Establishment of the Cellular Architecture of the Striatum," *J Neurosci.*, 2008, 28(3):622-632.
Barthelemy et al., "zhx-1: a novel mouse homeodomain protein containing two zinc-fingers and five homeodomains," *Biochem Biophys Res Commun.*, 1996, 224(3):870-876.
Bradley et al., "Formation of Germ-line Chimaeras from Embryo-Derived Teratocarcinoma Cell Lines," *Nature*, 1984, 309:255-258.
Brinster et al., "Factors affecting the efficiency of introducing foreign DNA into mice by microinjecting eggs," *PNAS USA*, 1985, 82:4438-4442.
Chen et al., "The Fezf2-Ctip2 genetic pathway regulates the fate choice of subcortical projection neurons in the developing cerebral cortex," *Proc Natl Acad Sci USA*, 2008, 105(32):11382-11387.
Evans et al., "Establishment in culture of pluripotential cells from mouse embryos," *Nature*, 1981, 292:154-156.
Feil et al., "Inducible Cre Mice," *Meth. Mol. Biol.*, 2009, 530:343-363.
Fukuda et al., "Potentiation of astrogliogenesis by STAT3-mediated activation of bone morphogenetic protein-Smad signaling in neural stem cells," *Mol. Cell Biol.*, Jul. 2007, 27(13):4931-4937.

(Continued)

*Primary Examiner* — John Ulm
(74) *Attorney, Agent, or Firm* — Fish & Richardson P.C.

(57) ABSTRACT

This disclosure describes a novel population of cerebellum-derived neural stem cells that can be isolated from the adult brain, expanded, and differentiated into neurons, astrocytes and oligodendrocytes. This disclosure also describes compositions and methods for producing oligodendrocytes. Oligodendrocytes can be produced in vitro (e.g., in culture) or in vivo (e.g., for therapy or in a non-human transgenic animal) using the compositions and methods described herein.

4 Claims, 15 Drawing Sheets

(56) References Cited

OTHER PUBLICATIONS

Gossler et al., "Transgenesis by means of blastocyst-derived embryonic stem cell lines," *PNAS USA*, 1986, 83:9065-9069.

Hanson et al., "Intranasal delivery bypasses the blood-brain barrier to target therapeutic agents to the central nervous system and treat neurodegenerative disease," *BMC Neurosci.*, 2008, 10:Supplem 3:S5.

Haruyama et al., "Overview: engineering transgenic constructs and mice," *Curr. Prot. Cell Biol.*, 2009, Ch. 19:Unit 19.10.

Hendricks et al., "Expression of the transcription factor GATA-3 is required for the development of the earliest T cell progenitors and correlates with stages of cellular proliferation in the thymus," *Eur. J. Immunol.*, 1999, 29:1912-1918

Jaenisch, "Transgenic animals," *Science*, 1988, 240:1468-1474.

Jahner et al., "De novo methylation and expression of retroviral genomes during mouse embryogenesis," *Nature*, 1982, 298:623-628.

Jahner et al., "Insertion of the bacterial *gpt* gene into the germ line of mice by retroviral infection," *PNAS USA*, 1985, 82;6927-6931.

Joshi et al., "Bhlhb5 regulates the postmitotic acquisition of area identities in layers II-V of the developing neocortex," *Neuron*, 2008, 60(2):258-272.

Klein et al., "Cerebellum- and forebrain-derived stem cells possess intrinsic regional character," *Develop.*, 2005, 132:4497-4508.

Kornack et al., "Cell proliferation without neurogenesis in adult primate neocortex," *Science*, 2001, 294:2127-2130.

Largaespada, "Transposon mutagenesis in mice," *Meth. Mol. Biol.*, 2009, 530:379-390.

Lee et al., "Isolation of neural stem cells from the postnatal cerebellum," *Nat. Neurosci,*, Jun. 2005, 8(6):723-729.

Mehler et al. "Developmental changes in progenitor cell responsiveness to bone morphogenetic proteins differentially modulate progressive CNS line age fate," *Dev. Neurosci.*, 2000, 22(1-2):74-85.

Modi et al.,"Nanotechnological applications for the treatment of neurodegenerative disorders," *Prog. Neurobiol.*, Aug. 2009, 88(4):272-285, Epub May 30, 2009.

Molyneaux et al., "Molecular development of corticospinal motor neuron circuitry," *Novartis Found Symp.*, 2007, 288:3-15.

Patel et al., "Getting into the brain: approaches to enhance brain drug delivery," *CNS Drugs*, 2009, 23:35-58.

Porteus and Baltimore, "Chimeric Nucleases Stimulate Gene Targeting in Human Cells," *Science*, 2003, 300(5620):763.

Robertson et al., "Germ-line transmission of genes introduced into cultured pluripotential cells by retroviral vector," *Nature*, 1986, 322:445-448.

Stewart et al., "Expression of retroviral vectors in transgenic mice obtained by embryo infection," *EMBO J*, 1987, 6:383-388.

Stolt et al., "SoxD proteins influence multiple stages of oligodendrocyte development and modulate SoxE protein function," *Dev Cell.* 2006, 11(5):697-709.

Sztriha et al., "Frameshift mutation of the zinc finger homeo box 1 B gene in syndromic corpus callosum agenesis (Mowat-Wilson syndrome)," *Neuropediatrics*, 2003, 34(6):322-325.

Towne et al., "Lentiviral and adeno-associated vector-based therapy for motor neuron disease through RNAi," *Meth. Mol. Biol.*, 2009, 555:87-108.

Van der Putten et al., "Efficient insertion of genes into the mouse germ line via retroviral vectors," *PNAS USA*, 1985, 82:6148-6152.

Authorized Officer Park, Jung Min, International Search Report & Written Opinion, International Application No. PCT/US2010/037789, mailed May 9, 2011,10 pages.

Authorized Officer Philippe Bécamel, International Report on Patentability, International Application No. PCT/US2010/037789, issued Dec. 12, 2011, 7 pages.

\* cited by examiner

SEQUENCE LISTING

<160> NUMBER OF SEQ ID NOS: 4

<210> SEQ ID NO 1
<211> LENGTH: 232

```
<212> TYPE: PRT
<213> ORGANISM: Homo sapiens

<400> SEQUENCE: 1

Met Glu Arg Cys Pro Ser Leu Gly Val Thr Leu Tyr Ala Leu Val Val
 1               5                  10                  15

Val Leu Gly Leu Arg Ala Thr Pro Ala Gly Gly Gln His Tyr Leu His
             20                  25                  30

Ile Arg Pro Ala Pro Ser Asp Asn Leu Pro Leu Val Asp Leu Ile Glu
         35                  40                  45

His Pro Asp Pro Ile Phe Asp Pro Lys Glu Lys Asp Leu Asn Glu Thr
     50                  55                  60

Leu Leu Arg Ser Leu Leu Gly Gly His Tyr Asp Pro Gly Phe Met Ala
 65                  70                  75                  80

Thr Ser Pro Pro Glu Asp Arg Pro Gly Gly Gly Gly Ala Ala Gly
                 85                  90                  95

Gly Ala Glu Asp Leu Ala Glu Leu Asp Gln Leu Leu Arg Gln Arg Pro
            100                 105                 110

Ser Gly Ala Met Pro Ser Glu Ile Lys Gly Leu Glu Phe Ser Glu Gly
            115                 120                 125

Leu Ala Gln Gly Lys Lys Gln Arg Leu Ser Lys Leu Arg Arg Lys
130                 135                 140

Leu Gln Met Trp Leu Trp Ser Gln Thr Phe Cys Pro Val Leu Tyr Ala
145                 150                 155                 160

Trp Asn Asp Leu Gly Ser Arg Phe Trp Pro Arg Tyr Val Lys Val Gly
                165                 170                 175

Ser Cys Phe Ser Lys Arg Ser Cys Ser Val Pro Glu Gly Met Val Cys
                180                 185                 190

Lys Pro Ser Lys Ser Val His Leu Thr Val Leu Arg Trp Arg Cys Gln
            195                 200                 205

Arg Arg Gly Gly Gln Arg Cys Gly Trp Ile Pro Ile Gln Tyr Pro Ile
            210                 215                 220

Ile Ser Glu Cys Lys Cys Ser Cys
225                 230

<210> SEQ ID NO 2
<211> LENGTH: 232
<212> TYPE: PRT
<213> ORGANISM: Mus musculus

<400> SEQUENCE: 2

Met Glu Arg Cys Pro Ser Leu Gly Val Thr Leu Tyr Ala Leu Val Val
 1               5                  10                  15

Val Leu Gly Leu Arg Ala Ala Pro Ala Gly Gly Gln His Tyr Leu His
             20                  25                  30

Ile Arg Pro Ala Pro Ser Asp Asn Leu Pro Leu Val Asp Leu Ile Glu
         35                  40                  45

His Pro Asp Pro Ile Phe Asp Pro Lys Glu Lys Asp Leu Asn Glu Thr
     50                  55                  60

Leu Leu Arg Ser Leu Leu Gly Gly His Tyr Asp Pro Gly Phe Met Ala
 65                  70                  75                  80

Thr Ser Pro Pro Glu Asp Arg Pro Gly Gly Gly Gly Pro Ala Gly
                 85                  90                  95

Gly Ala Glu Asp Leu Ala Glu Leu Asp Gln Leu Leu Arg Gln Arg Pro
            100                 105                 110

Ser Gly Ala Met Pro Ser Glu Ile Lys Gly Leu Glu Phe Ser Glu Gly
```

-continued

```
            115                 120                 125
Leu Ala Gln Gly Lys Lys Gln Arg Leu Ser Lys Leu Arg Arg Lys
            130                 135                 140
Leu Gln Met Trp Leu Trp Ser Gln Thr Phe Cys Pro Val Leu Tyr Ala
145                 150                 155                 160
Trp Asn Asp Leu Gly Ser Arg Phe Trp Pro Arg Tyr Val Lys Val Gly
                165                 170                 175
Ser Cys Phe Ser Lys Arg Ser Cys Ser Val Pro Glu Gly Met Val Cys
                180                 185                 190
Lys Pro Ser Lys Ser Val His Leu Thr Val Leu Arg Trp Arg Cys Gln
                195                 200                 205
Arg Arg Gly Gly Gln Arg Cys Gly Trp Ile Pro Ile Gln Tyr Pro Ile
210                 215                 220
Ile Ser Glu Cys Lys Cys Ser Cys
225                 230

<210> SEQ ID NO 3
<211> LENGTH: 202
<212> TYPE: PRT
<213> ORGANISM: Homo sapiens

<400> SEQUENCE: 3

Met Lys Val Leu Ala Ala Gly Val Val Pro Leu Leu Leu Val Leu His
1               5                   10                  15
Trp Lys His Gly Ala Gly Ser Pro Leu Pro Ile Thr Pro Val Asn Ala
                20                  25                  30
Thr Cys Ala Ile Arg His Pro Cys His Asn Asn Leu Met Asn Gln Ile
            35                  40                  45
Arg Ser Gln Leu Ala Gln Leu Asn Gly Ser Ala Asn Ala Leu Phe Ile
        50                  55                  60
Leu Tyr Tyr Thr Ala Gln Gly Glu Pro Phe Pro Asn Asn Leu Asp Lys
65                  70                  75                  80
Leu Cys Gly Pro Asn Val Thr Asp Phe Pro Pro Phe His Ala Asn Gly
                85                  90                  95
Thr Glu Lys Ala Lys Leu Val Glu Leu Tyr Arg Ile Val Val Tyr Leu
                100                 105                 110
Gly Thr Ser Leu Gly Asn Ile Thr Arg Asp Gln Lys Ile Leu Asn Pro
            115                 120                 125
Ser Ala Leu Ser Leu His Ser Lys Leu Asn Ala Thr Ala Asp Ile Leu
        130                 135                 140
Arg Gly Leu Leu Ser Asn Val Leu Cys Arg Leu Cys Ser Lys Tyr His
145                 150                 155                 160
Val Gly His Val Asp Val Thr Tyr Gly Pro Asp Thr Ser Gly Lys Asp
                165                 170                 175
Val Phe Gln Lys Lys Lys Leu Gly Cys Gln Leu Leu Gly Lys Tyr Lys
                180                 185                 190
Gln Ile Ile Ala Val Leu Ala Gln Ala Phe
            195                 200

<210> SEQ ID NO 4
<211> LENGTH: 178
<212> TYPE: PRT
<213> ORGANISM: Mus musculus

<400> SEQUENCE: 4

His Trp Lys His Gly Ala Gly Ser Pro Leu Pro Ile Thr Pro Val Asn
1               5                   10                  15
```

```
Ala Thr Cys Ala Ile Arg His Pro Cys His Gly Asn Leu Met Asn Gln
            20                  25                  30

Ile Lys Asn Gln Leu Ala Gln Leu Asn Gly Ser Ala Asn Ala Leu Phe
        35                  40                  45

Ile Ser Tyr Tyr Thr Ala Gln Gly Glu Pro Phe Pro Asn Asn Val Glu
        50                  55                  60

Lys Leu Cys Ala Pro Asn Met Thr Asp Phe Pro Ser Phe His Gly Asn
65                  70                  75                  80

Gly Thr Glu Lys Thr Lys Leu Val Glu Leu Tyr Arg Met Val Ala Tyr
                85                  90                  95

Leu Ser Ala Ser Leu Thr Asn Ile Thr Arg Asp Gln Lys Val Leu Asn
            100                 105                 110

Pro Thr Ala Val Ser Leu Gln Val Lys Leu Asn Ala Thr Ile Asp Val
            115                 120                 125

Met Arg Gly Leu Leu Ser Asn Val Leu Cys Arg Leu Cys Asn Lys Tyr
    130                 135                 140

Arg Val Gly His Val Asp Val Pro Pro Val Pro Asp His Ser Asp Lys
145                 150                 155                 160

Glu Ala Phe Gln Arg Lys Lys Leu Gly Cys Gln Leu Leu Gly Thr Tyr
                165                 170                 175

Lys Gln
```

ADULT CEREBELLUM-DERIVED NEURAL STEM CELLS AND COMPOSITIONS AND METHODS FOR PRODUCING OLIGODENDROCYTES

FEDERALLY SPONSORED RESEARCH OR DEVELOPMENT

This invention was made with government support under Grant No. NS048187 awarded by The National Institutes of Health. The government has certain rights in the invention.

CROSS-REFERENCE TO RELATED APPLICATIONS

This application is a National Stage application under 35 U.S.C. §371 and claims benefit under 35 U.S.C. §119(a) of International Application No. PCT/US2010/037789 having an International Filing Date of Jun. 8, 2010, which claims the benefit of priority under 35 U.S.C. §119(e) of U.S. Application No. 61/184,972, filed Jun. 8, 2009 and 61/185,088, filed on Jun. 8, 2009. The disclosures of the prior applications are incorporated by reference in their entirety.

TECHNICAL FIELD

This disclosure relates to adult cerebellum-derived neural stem cells. This disclosure also relates to compositions and methods for producing oligodendrocytes.

BACKGROUND

Reports of cerebellar neural stem cells (NSCs) came initially from studies of postnatal day 7 (neurogenic) brain (Kornack et al., 2001, *Science*, 294:2127-2130); the source was suggested to be scattered prominin1+ cells in the white matter. Klein et al. (2005, *Develop.*, 132:4497-508) described cells derived from cerebellum capable of forming neurospheres with stage-restricted multilineage differentiation capacity.

Much attention is focused on developing therapies to promote oligodendrocyte differentiation or to transplant oligodendrocytes or oligodendrocyte progenitors to remyelinate damaged areas and restore function in the central nervous system. NSCs can be isolated from fetal or adult brain and can act as a source of myelinating transplants but, for greatest efficacy, these cells must first be directed to the oligodendrocyte progenitor (OP) pathway. Currently, there are limited methods for stimulating the production of oligodendrocytes. For example, there are reports in the literature that retinoic acid can induce embryonic stem cells to differentiate into oligodendrocytes, that gamma-secretase can direct cells down the OP pathway, and that ciliary neurotrophic factor (CNTF) appears to be involved in the maturation of oligodendrocytes, which results in an increase in myelin formation.

SUMMARY

This disclosure describes a novel population of cerebellum-derived neural stem cells that can be isolated from the adult brain, expanded, and differentiated into neurons, astrocytes and oligodendrocytes. This disclosure also describes compositions and methods for producing oligodendrocytes. Oligodendrocytes can be produced in vitro (e.g., in culture) or in vivo (e.g., for therapy or in a non-human transgenic animal) using the compositions and methods herein.

In one aspect, a substantially pure population of adult cerebellum-derived neural stem cells (NSCs) is provided. Such adult cerebellum-derived NSCs express the markers Sox1, Sox3, Sox9, BLBP, and nestin, which are down-regulated under differentiation conditions. The adult cerebellum-derived NSCs described herein are capable of differentiating into neurons, astrocytes, and oligodendrocytes. Following differentiation, the neurons express the marker Tuj1+, the astrocytes express the marker GFAP+, and the oligodendrocytes express the marker MBP+.

In another aspect, a method of repairing or regenerating neural tissue in the absence of teratoma production in a patient is provided. Such methods generally include administering the adult cerebellum-derived NSCs described herein to the patient. Following the administration step, the adult cerebellum-derived NSCs described herein express the markers MBP, calbindin, O4, and neurotransmitters such as GABA and glutamine. For example, lesion size and/or function (restoration of) can be evaluated before and after the administration step. In one embodiment, the administering step includes injecting the adult cerebellum-derived NSCs described herein into the patient. Such methods can be useful for a patient who has a CNS injury, a SCI injury, or has had a stroke.

In one aspect, a composition that includes noggin polypeptide or an active fragment thereof and Leukemia inhibitory factor (LIF) polypeptide or an active fragment thereof is provided. In some embodiments, the noggin polypeptide or an active fragment thereof is present at a concentration of about 20 to about 1000 ng per ml of an aqueous solution, and the LIF polypeptide or an active fragment thereof is present at a concentration of about 1 to about 20 mg per ml of an aqueous solution.

Representative sources for a noggin polypeptide or an active fragment thereof is human and mouse. A representative human noggin polypeptide has the amino acid sequence shown in SEQ ID NO:1 (corresponding to Accession No. NP_005441), and a representative mouse noggin polypeptide has the amino acid sequence shown in SEQ ID NO:2 (corresponding to Accession No. NM_008711.2). Representative sources for a LIF polypeptide or an active fragment thereof is human and mouse. A representative human LIF polypeptide has the amino acid sequence shown in SEQ ID NO:3 (corresponding to Accession No. NP_002300), and a representative mouse LIF polypeptide has the amino acid sequence shown in SEQ ID NO:4 (corresponding to Accession No. X06381.1).

In another aspect, an article of manufacture is provided that includes an inhaler. As described herein, the inhaler includes noggin polypeptide or an active fragment thereof. In some embodiments, the inhaler can further include LIF polypeptide or an active fragment thereof.

In yet another aspect, a method of inducing stem cells to differentiate into oligodendrocytes is provided. Such methods can include, for example, contacting stem cells with noggin polypeptide or an active fragment thereof. Examples of stem cells include, without limitation, neural stem cells and embryonic stem cells. Representative sources of noggin polypeptide or an active fragment thereof is a mouse or a human. Such methods further can include contacting the stem cells with LIF polypeptide or a fragment thereof. Representative sources of LIF polypeptide or an active fragment thereof is a mouse or a human.

In one embodiment, the noggin polypeptide or active fragment thereof is administered simultaneously with the LIF polypeptide or active fragment thereof. In another embodiment, the noggin polypeptide or active fragment thereof and the LIF polypeptide or active fragment thereof are administered sequentially. In certain instances, the stem cells are in culture; in other instances, the stem cells are in vivo. Under some circumstances, the contacting takes place in culture; under other circumstances, the contacting takes place in vivo.

In still another aspect, a method of inducing myelination in a patient suffering from demyelination is provided. Such a method includes administering an effective amount of noggin polypeptide or an active fragment thereof to the patient. Such methods also can include administering an effective amount of LIF polypeptide or an active fragment thereof to the patient. As indicated herein, the noggin and LIF can be administered simultaneously or sequentially. A representative route of administration is nasal inhalation. Demyelination can be due to, without limitation, a disease selected from the group consisting of multiple sclerosis, stroke, inflammation, and an autoimmune disease or an injury selected from the group consisting of spinal cord injury and traumatic brain injury.

In one aspect, a non-human transgenic animal is provided. Typically, the non-human transgenic animal has a nucleic acid construct, wherein the construct comprises a nucleic acid encoding a noggin polypeptide or an active fragment thereof operably linked to a promoter element that drives expression in central nervous system (CNS) progenitor cells operably linked to an inducible element. Such a non-human transgenic animal can be induced to express noggin in CNS progenitor cells.

In one embodiment, the element that drives expression in CNS progenitor cells is nestin (e.g., intron II from nestin). In one embodiment, the inducible element is a tetracycline or tetracycline-derivative inducible element. A representative non-human transgenic animal is a mouse.

In one aspect, a method of producing oligodendrocytes is provided. Such methods generally include culturing stem cells in the presence of noggin polypeptide or an active fragment thereof. Such methods further can include culturing the stem cells in the presence of LIF polypeptide or an active fragment thereof. As indicated herein, representative stem cells include neural stem cells or embryonic stem cells.

In another aspect, a method of producing oligodendrocytes is provided. Such a method can include administering, to a non-human transgenic animal as described herein, an agent that induces the inducible element to express the noggin polypeptide. In one embodiment, the administration is via the animal's drinking water.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DETAILED DESCRIPTION

Figure 1:
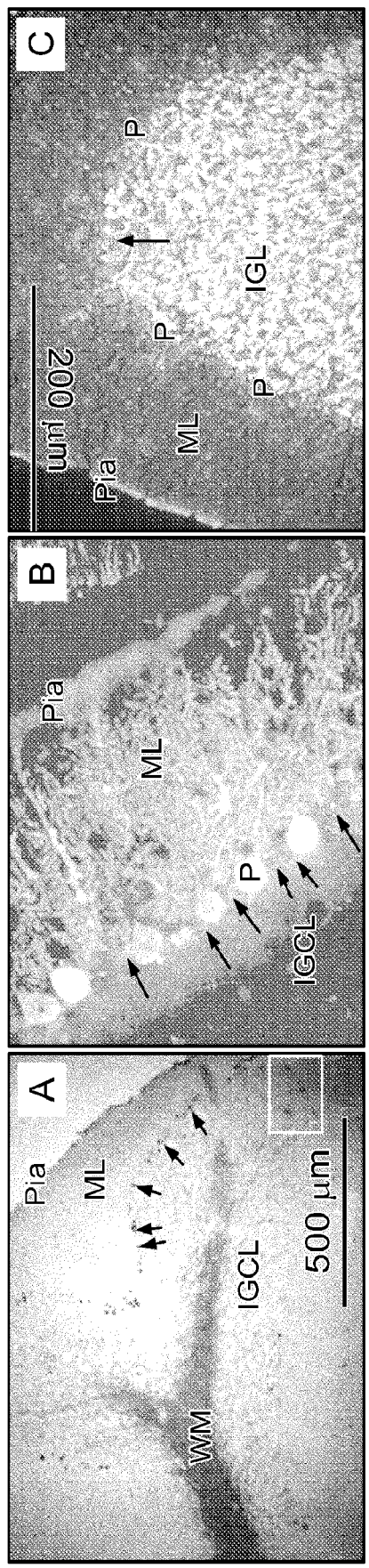
FIG. 1 illustrates β-gal expression in a population of cells at the interface of the molecular layer (ML) and internal granule cell layer (IGCL) in the cerebellar cortex. (B) A population of cells in the Purkinje cell layer expresses eGFP, noggin and BG markers (Sox3, arrows). WM=white matter. P=Purkinje cells, α-calbindin IHC. (C) After noggin induction, BrdU+BG cells were present in the Purkinje cell layer (arrow).

This disclosure describes a novel, substantially pure population of cerebellum neural stem cells (NSCs) that can be obtained from the adult brain, expanded, and differentiated into neurons, astrocytes, and oligodendrocytes. A "substantially pure population" of cells means that at least about 70% (e.g., about 75%, 80%, 85%, 90%, 95%, 99% or 100%) of the cells present (e.g., in the absence of feeder layer cells) are adult cerebellum-derived NSCs as described herein or cells differentiating therefrom. In addition, methods are available for further increasing the number of adult cerebellum-derived NSCs in a population. For example, methods such as FACS or methods that use magnetic bead technology can be used to purify one or more subpopulations of adult cerebellum-derived NSCs for further expansion.

This disclosure also describes compositions and methods for producing oligodendrocytes. The production of oligodendrocytes in vitro (e.g., in culture) is described herein. In addition, the production of oligodendrocytes in vivo is described herein. Oligodendrocytes can be produced in vivo for therapeutic purposes (e.g., for treating demyelinating diseases or injuries), or oligodendrocytes can be produced in vivo using a non-human transgenic animal such as those described herein.

Neural Stem Cells

Adult Cerebellum-Derived NSCs

The adult cerebellum-derived NSCs described herein differ from other previously described adult cerebellum—or otherwise-derived NSCs. Stem cells generally are considered to be undifferentiated when, for example, protein expression and the capacity for multi-lineage differentiation in clonal analysis in vitro. The adult cerebellum-derived NSCs described herein can be used to generate neurons, astrocytes and oligodendrocytes. In an undifferentiated and uncommitted state, adult cerebellum-derived NSCs express Sox1, Sox3, Sox9, BLBP, and nestin. When the adult cerebellum-derived NSCs described herein are cultured in defined medium (DMEM/F12 including N2 supplement and 1% fetal bovine serum (FBS), the cells begin differentiating into neurons, which express Tuj1+; when the adult cerebellum-derived NSCs described herein are cultured in DMEM/F12 including F2 supplement and 1% FBS, the cells begin differentiating into astrocytes, which express GFAP+; and when the adult cerebellum-derived NSCs described herein are cultured in DMEM/F12 including F2 supplement, 1% FBS, noggin and, optionally, LIF, the cells begin differentiating into oligodendrocytes, which express MBP+, Olig2, and NG2.

When NSCs derived from the adult cerebellar cortex are grown under clonal conditions, individual cells can form neurospheres (indicating their ability to self-renew), and, when grown in adherent culture in defined medium containing N2 salts, neurospheres have the ability to differentiate into Tuj1+ neurons, GFAP+ astrocytes, and Olig2+, MBP+ oligodendroglia. In the presence of noggin, the percentage of neurons in these cultures increases, and the further addition of LIF to the culture can significantly increase the numbers of MBP+ oligodendrocytes.

Under differentiation conditions, markers characteristic of neural stem cells (e.g., Sox1, Sox3, Sox9, and/or nestin) typically are downregulated, while the appropriate cell line specific markers are upregulated. As used herein, differentiation culture conditions refer to conditions under which the adult cerebellum-derived NSCs form differentiated derivatives and can be in the presence of, for example, growth factors and/or other differentiated or undifferentiated cell types.

It is understood by those in the art that the markers used to describe the phenotype of adult cerebellum-derived NSCs generally refer to a protein or a nucleic acid encoding such a protein that can be detected by any number of methods. For example, FACS can be used to detect a cell-surface protein, PCR (e.g., RT-PCR) can be used to detect the presence or absence of a RNA transcript encoding a protein (e.g., a nuclear transcription factor), Western blotting can detect and measure the quantity of a polypeptide, and immunohistochemistry can be used to detect the presence, absence and/or pattern of distribution of a protein in a cell.

It is also understood by those in the art that the presence or absence of markers expressed in or on cells can vary when cells are grown under different culture conditions. The markers used to describe the adult cerebellum-derived NSCs were detected under standard culturing conditions. For example, standard culturing conditions for the adult cerebellum-derived NSCs described herein can include isolating the cells from adult cerebellar cortex by disaggregation, followed by growth in suspension culture (in DMEM/F12 with N2, glutamine, heparin, EGF, and FGF2) at 37° C. with 5% $CO_2$. Under these conditions, the adult cerebellum-derived NSCs form neurospheres. Alternatively, cells can be FACSorted based on the binding of the fluorogenic β-gal substrate, fluorescein di-(beta)-D-galactopyranoside), followed by clonal growth. For differentiation, neurospheres grown for 7 days can be disaggregated manually and plated on poly-ornithine coated dishes containing DMEM/F12 with N2 and 1% fetal bovine serum. After about 7 days in culture, cells can be fixed and inmunostained for neuronal, glial and/or oligodendrocyte markers.

Methods of Making and Using Adult Cerebellum-Derived NSCs

The cells described herein can be obtained by mechanically and enzymatically dissociating cells from the cerebellum portion of a mammalian (e.g., rodent or human) adult brain. Mechanical dissociation can be brought about by methods that include, without limitation, chopping and/or mincing the tissue, and/or centrifugation and the like. Enzymatic dissociation from the ECM and/or from cell-to-cell associations can be brought about by solutions lacking calcium and magnesium and in the presence of enzymes including but not limited to collegenase and trypsin. A population of adult cerebellum-derived NSCs can be expanded on a mesenchymal feeder monolayer. A mesenchymal feeder monolayer can be commercially prepared. The adult cerebellum-derived NSCs typically are loosely attached to the monolayer and can be collected in the medium (e.g., in the supernatant). As used herein, "expansion" refers to increasing the number of cells under conditions in which the cells do not undergo a significant amount of differentiation.

The cells described herein are capable of repair or regeneration of, for example, central nervous system (CNS) injuries, spinal cord injuries (SCI), infections, or stroke. The cells described herein can be used to treat or repair injured or damaged tissue and also can be used to provide insight into neural growth and regeneration. It is understood by those in the art that the terms treating, repairing, replacing, augmenting, improving, rescuing, repopulating or regenerating are used synonymously with respect to disease or damaged tissue.

Introducing cells into a patient may be accomplished by any means known in the medical arts, including but not limited to grafting and injection. The cells can be introduced with or without a natural or artificial support, matrix, or polymer. It should be understood that adult cerebellum-derived NSCs can be injected or grafted into or at a site separate and/or apart from the diseased or damaged tissue and allowed to migrate.

As those of skill in the art would understand, a number of factors may be determinative of when and how a stem or progenitor cell differentiates. As a result, it may be desirable to induce differentiation of the cells described herein in a controlled manner and/or by employing factors that are not easily or desirably introduced into a patient. Therefore, the cells described herein can be induced to differentiate prior to being introduced into the patient by, for example, in vitro exposure to extracellular and/or intracellular factors such as noggin, retinoic acid, leukemia inhibitory factor, and the removal of mitogens (fibroblast growth factors, EGF, etc.) from the medium.

Compositions and Methods for Producing Oligodendrocytes

Also described herein are compositions and methods for producing oligodendrocytes from stem cells (e.g., adult cerebellum neural stem cells). Compositions that include noggin and optionally, LIF, can be used to produce oligodendrocytes. Such compositions can be used in therapeutic methods to produce oligodendrocytes.

Noggin

The secreted polypeptide noggin, encoded by the NOG gene (also called the SYM1 gene or the SYNS1 gene in humans), binds and inhibits signaling by members of the transforming growth factor (TGF)-beta superfamily signaling proteins. The gene encoding noggin was originally isolated from *Xenopus* based on its ability to restore normal dorsal-ventral body axis in embryos that had been artificially ventralized by UV treatment. A mouse knockout of noggin suggests that noggin is involved in numerous developmental processes including neural tube fusion and joint formation. The amino acid sequence of human noggin is highly homologous to that of *Xenopus*, rat and mouse. Noggin is post-translationally modified, and is secreted as a disulfide-bonded homodimer. The coding sequence for human noggin is contained within a single exon.

Representative examples of noggin sequences include, but are not limited to: GenBank Accession Nos. EAW94528 and AAH34027 disclosing amino acid sequences of noggin polypeptides from human (*Homo sapiens*); GenBank Accession Nos. NP_032737 and AAB38281 disclosing amino acid sequences of noggin polypeptides from mouse (*Mus musculus*); GenBank Accession No. NP_037122 disclosing an amino acid sequence of a noggin polypeptide from rat (*Rattus norvegicus*); GenBank Accession No. NP_001079113 disclosing an amino acid sequence of a noggin polypeptide from *Xenopus laevis*; GenBank Accession No. NP_989454 disclosing an amino acid sequence of a noggin polypeptide from chicken (*Gallus gallus*); and GenBank Accession No. NP_001137163 disclosing an amino acid sequence of a noggin polypeptide from pig (*Sus scrofa*). Additional sequences of noggin polypeptides can be obtained from a database using, for example, a search query such as "noggin".

As used herein, "an active fragment thereof" refers to a polypeptide having at least functional noggin activity. Active fragments of noggin polypeptides can be screened by injecting a mRNA encoding the fragment of the noggin polypeptide into, for example, the marginal zone of a single ventral blastomere of a four-cell Xenopus embryo and evaluating the embryo at the tailbud stage for the presence of secondary axes. The presence of the secondary axes at the tailbud stage indicates that the fragment possess functionality.

NOG nucleic acids refer to nucleic acid sequences that encode a functional noggin polypeptide as described above. NOG nucleic acid sequences can include those that encode only the residues required for an active fragment or can include sequences corresponding to the entire coding sequence. NOG nucleic acid sequences can be obtained by known methods (e.g., searching a database, or cross-referencing from the above-identified noggin polypeptides). A representative NOG nucleic acid sequence encoding a human noggin polypeptide includes GenBank Accession No. NM_005450; a representative NOG nucleic acid sequence encoding a mouse noggin polypeptide includes GenBank Accession No. NM_008711; a representative NOG nucleic acid sequence encoding a *Xenopus laevis* noggin polypeptide includes GenBank Accession No. BC 169672; and a representative NOG nucleic acid sequence encoding a rat noggin polypeptide includes GenBank Accession No. NM_012990. Alternatively, the sequence of a noggin polypeptide (e.g., GenBank Accession No. AAH34027) can be used to design a NOG nucleic acid.

Leukemia Inhibitory Factor (LIF)

Leukemia inhibitory factor, or LIF, an interleukin 6 class cytokine, is a polypeptide present in cells that affects their growth and development. LIF derives its name from its ability to induce the terminal differentiation of myeloid leukemic cells. Other properties attributed to LIF include, for example, the growth promotion and cell differentiation of various types of target cells, influence on bone metabolism, cachexia, neural development, embryogenesis and inflammation. LIF is normally expressed in the trophectoderm of the developing embryo, with its receptor, LIFR, expressed throughout the inner cell mass. Since embryonic stem cells (ESCs) are derived from the inner cell mass at the blastocyst stage, removing ESCs from the inner cell mass removes their source of LIF. Removal of LIF from cell culture of mouse stem cells causes those stem cells to differentiate.

Representative examples of LIF sequences include, but are not limited to: GenBank Accession Nos. AAA51699, AACO5174, and AAH93733 disclosing amino acid sequences of LIF polypeptides from human (*Homo sapiens*); GenBank Accession Nos. CAI25201 and CAA00190 disclosing amino acid sequences of LIF polypeptides from mouse (*Mus musculus*); GenBank Accession No. BAA19511 disclosing an amino acid sequence of a LIF polypeptide from cattle (*Bos taurus*); GenBank Accession Nos. BAA31357 and EDM00223 disclosing amino acid sequences of LIF polypeptides from rat (*Rattus norvegicus*); and GenBank Accession No. NP_999567 disclosing an amino acid sequence of a LIF polypeptide from pig (*Sus scrofa*). Additional sequences of LIF polypeptides can be obtained from a database using, for example, a search query such as "leukemia inhibitory factor" or "LIF".

As used herein, "an active fragment thereof" refers to a polypeptide having at least functional LIF activity. Fragments of LIF polypeptides can be screened for functionality (i.e., active fragments can be identified) by introducing the polypeptide fragment into a culture of mouse ESC and evaluating the ability of the polypeptide fragment to activate Stat3 signaling and to maintain the undifferentiated character of the ESC.

Nucleic acid sequences can include those that encode only the residues required for an active fragment or can include sequences corresponding to the entire coding sequence. Nucleic acid sequences encoding LIF polypeptides can be obtained by known methods (e.g., searching a database, or cross-referencing from the above-identified LIF polypeptides). Representative nucleic acid sequences encoding human LIF polypeptides include GenBank Accession Nos. NM_002309, BC069540, and BC093733; representative nucleic acid sequences encoding mouse LIF polypeptides include GenBank Accession Nos. NM_008501 and AF065917; representative nucleic acid sequences encoding rat LIF polypeptides include GenBank Accession Nos. NM_022196 and NM_031048; a representative nucleic acid sequence encoding a LIF polypeptide from cattle include GenBank Accession No. U65394; and a representative nucleic acid sequence encoding a pig LIF polypeptide includes GenBank Accession No. NM_214402. Alternatively, the sequence of a LIF polypeptide (e.g., GenBank Accession No. AAA51699) can be used to design the corresponding nucleic acid.

Polypeptides and Nucleic Acids

As used herein, "purified polypeptide" refers to a polypeptide that has been removed from its natural environment, i.e., it has been separated from cellular components that naturally accompany it. Typically, a polypeptide is purified when it is at least 60% (e.g., 70%, 80%, 90%, 95%, or 99%), by weight, free from proteins and molecules that are naturally associated with it. As used herein, "isolated nucleic acid" refers to a nucleic acid corresponding to part or all of a gene encoding a polypeptide, but free of sequences that normally flank one or both sides of the wild-type gene in a naturally occurring genome. The term "isolated" as used herein with respect to nucleic acids also includes any non-naturally-occurring nucleic acid sequence since such non-naturally-occurring sequences are not found in nature and do not have immediately contiguous sequences in a naturally-occurring genome. Thus, an isolated nucleic acid includes, without limitation, a DNA molecule that exists as a separate molecule (e.g., a cDNA or genomic DNA fragment produced by PCR or restriction endonuclease digestion), as well as recombinant DNA that is incorporated into a vector, an autonomously replicating plasmid, a virus (e.g., a retrovirus, adenovirus, or herpes virus) or into the genomic DNA of a prokaryote or eukaryote. A nucleic acid existing among hundreds to millions of other nucleic acids within, for example, cDNA libraries or genomic libraries, or gel slices containing a genomic DNA restriction digest, is not to be considered an isolated nucleic acid.

Vectors, including expression vectors, are commercially available and/or produced by recombinant DNA technology methods routine in the art. A vector containing a nucleic acid additionally can have elements necessary for expression operably linked to such a nucleic acid, and further can include sequences such as those encoding a selectable marker (e.g., an antibiotic resistance gene), and/or those that can be used in purification of an encoded polypeptide (e.g., 6× His tag). Elements necessary for expression include nucleic acid sequences that direct and regulate expression of coding sequences. One example of an element necessary for expression is a promoter sequence. Elements necessary for expression also can include introns, enhancer sequences, response elements, or inducible elements that modulate expression of a nucleic acid. As used herein, operably linked means that a promoter and/or other regulatory element(s) are positioned in a vector relative to a coding sequence in such a way as to direct or regulate expression of the coding sequence. Elements necessary for expression can be of bacterial, yeast, insect, mammalian, or viral origin and vectors can contain a combination of elements from different origins. Many methods for introducing vectors into cells, both in vivo and in vitro, are well known to those skilled in the art and include, without limitation, calcium phosphate precipitation, electroporation, heat shock, lipofection, microinjection, and viral-mediated nucleic acid transfer.

Nucleic acid molecules (DNA or RNA) can be isolated by standard techniques. Isolated nucleic acids can be obtained using any method including, without limitation, common molecular cloning and chemical nucleic acid synthesis techniques. For example, polymerase chain reaction (PCR) techniques can be used to obtain an isolated nucleic acid. PCR can be used to amplify specific sequences from DNA as well as RNA, including sequences from total genomic DNA or total cellular RNA. General PCR techniques are described, for example in *PCR Primer: A Laboratory Manual*, Dieffenbach & Dveksler, Eds., Cold Spring Harbor Laboratory Press, 1995. Nucleic acids also can be chemically synthesized, either as a single nucleic acid molecule or as a series of oligonucleotides.

Furthermore, nucleic acid hybridization techniques (e.g., Southern blotting, Northern blotting) can be used to identify or isolate a nucleic acid. Briefly, a nucleic acid sequence encoding a polypeptide can be used as a probe to identify a similar nucleic acid by hybridization under conditions of moderate to high stringency. Moderately stringent hybridization conditions include hybridization at about 42° C. in a hybridization solution containing 25 mM $KPO_4$ (pH 7.4), 5×SSC, 5× Denhart's solution, 50 µg/mL denatured, sonicated salmon sperm DNA, 50% formamide, 10% Dextran sulfate, and 1-15 ng/mL probe (about $5 \times 10^7$ cpm/µg), and wash steps at about 50° C. with a wash solution containing 2×SSC and 0.1% SDS. For high stringency, the same hybridization conditions can be used, but washes are performed at about 65° C. with a wash solution containing 0.2×SSC and 0.1% SDS. See, for example, sections 7.39-7.52 of Sambrook, Fritsch & Maniatis, *Molecular Cloning: A Laboratory Manual*, 2nd Ed., 1989, Cold Spring Harbor Laboratory Press, Plainview, N.Y.

Mutant nucleic acids that encode mutant polypeptides also can be used in the present compositions provided that the encoded mutant polypeptide exhibits functional activity. Types of mutations that a nucleic acid can carry include, without limitation, insertions, deletions, transitions, transversions and inversions. A nucleic acid can include more than one mutation and more than one type of mutation. Such mutations, if present within the coding sequence, can result in insertions or deletions of one or more amino acids into a polypeptide, conservative or non-conservative amino acid substitutions within a polypeptide or premature termination of a polypeptide.

Compositions and Methods for Producing Oligodendrocytes

The compositions described herein can be used in a method of producing oligodendrocytes. Oligodendrocytes are a type of neuroglial cell with dendritic projections that coil around axons of neural cells. The projections continue as myelin sheaths over the axons in the central nervous system of higher vertebrates. A single oligodendrocyte can extend to up to 50 axons, wrapping around approximately 1 mm of each and forming the myelin sheath. As part of the nervous system, oligodendrocytes are closely related to nerve cells and, like all other glial cells, the oligodendrocytes have a supporting role towards neurons. However, oligodendrocytes are intimately involved in signal propagation as follows. The nervous system of mammals crucially depends on the myelin sheath for insulation as the myelin sheath results in decreased ion leakage and lower capacitance of the cell membrane. Myelin also results in an overall increase in impulse speed as saltatory propagation of action potentials occurs at the nodes of Ranvier in between Schwann cells (of the peripheral nervous system) and oligodendrocytes (of the CNS). Furthermore, miniaturization occurs, where the impulse speed of myelinated axons increases linearly with the axon diameter, while the impulse speed of unmyelinated cells increases only with the square root of the axon diameter.

Oligodendroglia arise during development from an oligodendrocyte precursor cell, which can be identified by its expression of a number of cell-surface antigens, including the ganglioside GD3, the NG2 chondroitin sulfate proteoglycan, and the platelet-derived growth factor-alpha receptor subunit PDGF-alphaR. In rodent, the majority of oligodendroglial progenitors arise during late embryogenesis and early postnatal development from restricted periventricular germinal regions. Initially, the oligodendrocyte precursor cells migrate away from this germinal region to populate both developing white and gray matter, where they differentiate and mature into myelin-forming oligodendroglia.

For example, stem cells (e.g., adult cerebellum neural stem cells) can be cultured in the presence of noggin polypeptide or an active fragment thereof, which will result in their differentiation into oligodendrocytes. In certain instances, LIF can be added to the culture, which results in increased numbers of oligodendrocytes. The combination of noggin and LIF seems to have a synergistic effect on the differentiation of stem cells into oligodendrocytes. Thus, as described herein, noggin polypeptides or active fragments thereof, optionally in the presence of LIF polypeptides or active fragments thereof, can be used to induce stem cells to differentiate into oligodendrocytes. As used herein, stem cells can be embryonic stem cells (ESC) or, for example, nervous system progenitor cells (e.g., neural stem cells (e.g., adult cerebellum neural stem cells)).

Because of the ability of noggin and, optionally, LIF to cause the differentiation of stem cells (e.g., adult cerebellum neural stem cells) into oligodendrocytes, noggin and, optionally, LIF, can be used to induce myelination in a patient suffering from demyelination. That is, an effective amount of noggin polypeptide or an active fragment thereof can be administered to a patient in order to stimulate oligodendrocyte production. Optionally, an effective amount of LIF polypeptide or an active fragment thereof can be administered to the patient to further stimulate oligodendrocyte production.

A patient can suffer from demyelination for a number of reasons including, without limitation, disease, aging, and injury. Demyelinating diseases include, for example, multiple sclerosis and leukodystrophies. Demyelinating injuries include, for example, cerebral palsy (periventricular leukomalacia), which is caused by damage to developing oligodendrocytes in the brain areas around the cerebral ventricles, spinal cord injury, and stroke. Oligodendrocyte dysfunction can occur because of inflammation or infection (e.g., viral infection) and also may be implicated in the pathophysiology of schizophrenia and bipolar disorder.

Noggin or noggin and LIF can be administered by any number of methods, provided that the protein(s) are eventually delivered to the CNS. One of the most effective ways of delivery to the CNS is nasal inhalation (see, for example, Hanson et al., 2008, *BMC Neurosci.*, 10:Supplem 3:S5), as discussed above, although other methods may prove to be useful as well. For example, proteins can be directly injected (see, for example, Towne et al., 2009, *Meth. Mol. Biol.*, 555: 87-108) or delivered using nanoparticles (see, for example, Modi et al., 2009, *Prog. Neurobiol.*, e-pub on May 29, 2009). See, also, Patel et al. (2009, *CNS Drugs*, 23:35-58) for a review of drug delivery to the brain.

Articles of Manufacture

This disclosure provides for an article of manufacture that includes an inhaler. As is known in the art, an inhaler is a device used to deliver drugs or medication in the form of a spray that is inhaled through the nose or the mouth. The most common form of inhaler is the metered dose inhaler (MDI), which delivers a precise amount with each inhaled puff.

In one embodiment, an inhaler can contain 20-1000 ng of noggin polypeptide or active fragment thereof per ml of saline solution. An inhaler can contain the disulfide-bonded homodimer of the noggin polypeptide or an active fragment thereof, or an inhaler can contain noggin polypeptides and active fragments thereof that can spontaneously homodimerize. In another embodiment, an inhaler can contain 1-20 ng of LIF per ml of saline solution. Since both noggin and LIF are soluble in aqueous solutions, they can be readily combined in a single inhaler. In one embodiment, 12 ng LIF polypeptide or active fragments thereof per kg of body weight and 400 ng noggin polypeptide or active fragments thereof per kg body weight can be administered using, for example, an inhaler as described herein.

Transgenic Animals

This disclosure describes non-human transgenic animals having a nucleic acid sequence in their genome that encodes a noggin polypeptide or an active fragment thereof. In the non-human transgenic animals described herein, the nucleic acid encoding the noggin polypeptide or active fragment thereof is under the control of (i.e., operably linked to) a promoter element that drives expression of the nucleic acid in central nervous system (CNS) progenitor cells. In addition, in the non-human transgenic animals described herein, the promoter element is operably linked to an inducible element such that the non-human transgenic animal can be induced to express noggin in CNS progenitor cells. The transgenic animals can be used to isolate quantities of neural stem cells to produce oligodendrocytes or to study CNS development and the role of oligodendrocytes (e.g., in various tissues at different developmental times).

A variety of vectors useful for the construction of transgenic animals are well known and used in the art. The choice of vector is often dependent on the targeting strategy, the selection strategy, and whether and what elements necessary for expression are required or desired to express the encoded protein. The non-human transgenic animals described herein have both a promoter element and an inducible element. Typically, it is desirable that the promoter element is a neural cell-specific promoter element such as one that drives expression in CNS progenitor cells. A representative promoter is the nestin promoter exemplified herein, while another promoter element that can be used is the promoter from the brain lipid binding protein (BLBP). Inducible elements are known in the art and include the tetracycline (or derivative thereof)—inducible promoter exemplified herein, the Tet-on or Tet-off system (see, for example, Haruyama et al., 2009, *Curr. Prot. Cell Biol.*, Ch. 19), transposons (see, for example, Largaespada, 2009, *Meth. Mol. Biol.*, 530:379-90), or the Cre recombinase system such as the tamoxifen-dependent Cre recombinase (Feils et al., 2009, *Meth. Mol. Biol.*, 530:343-63).

As used herein, a "transgenic" animal means any non-human animal having one of the various forms of genetic alterations used in the art including application of gene-targeting by homologous recombination at defined locations in the genome, random integration, so-called knock-in (KI), knock-out (KO), or alternatively transgenes [plasmids, YACs, BACs] incorporated at various locations in the genome. The methods used for generating transgenic mice are well known to one of skill in the art. See, Nagy et al., 2002, "Manipulating the Mouse Embryo: A Laboratory Manual," 3$^{rd}$ Ed., Cold Spring Harbor Laboratory Press, and U.S. Pat. No. 4,736,866 for exemplary methods for the production of a transgenic mouse. Further, the genetic transformation of various types of organisms is disclosed and described in detail in U.S. Pat. No. 4,873,191.

Without meaning to be exhaustive, the following is a representative list of references relevant to methods of generating a non-human transgenic animal. See, for example, Brinster et al., 1985, *PNAS USA,* 82:4438-4442; Jahner et al., 1985, *PNAS USA,* 82; 6927-6931; Van der Putten et al., 1985, *PNAS USA,* 82:6148-6152; Stewart et al., 1987, *EMBO J,* 6:383-388; Jahner et al., 1982, *Nature,* 298:623-628; Porteus & Baltimore, 2003, *Science,* 300(5620):763; Evans et al., 1981, *Nature,* 292:154-156; Bradley et al., 1984, *Nature,* 309:255-258; Gossler et al., 1986, *PNAS USA,* 83:9065-9069; Robertson et al., 1986, *Nature,* 322:445-448; and Jaenisch, 1988, *Science,* 240:1468-1474.

Once a transgenic animal has been created, it is a routine matter to cross-breed the animal with other transgenic animals to produce animals homozygous for the transgene, or multi-genic animals, i.e., animal models carrying multiple transgenes or genetic alterations. The non-human transgenic animals described herein, and tissues and cell lines derived therefrom, can be utilized in screens for compounds that affect the pathways in which the transgenes are involved. For example, a non-human transgenic animal as described herein can be used to identify novel downstream targets or pathways involved in oligodendrocyte differentiation and neuroblast formation. Additionally, the synergy of other compounds or small molecules with noggin in lineage differentiation can be examined in a non-human transgenic animal as described herein. In addition, the non-human transgenic animal described herein that is inducible for noggin production can be used to produce oligodendrocytes. For example, the non-human transgenic animal can be contacted with an agent that induces the inducible element to produce noggin and, if desired, further contacted with LIF.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Section A. Neural Stem Cell Analysis

Example 1

Adult Cerebellum-Derived Neural Stem Cells

Figure 2:
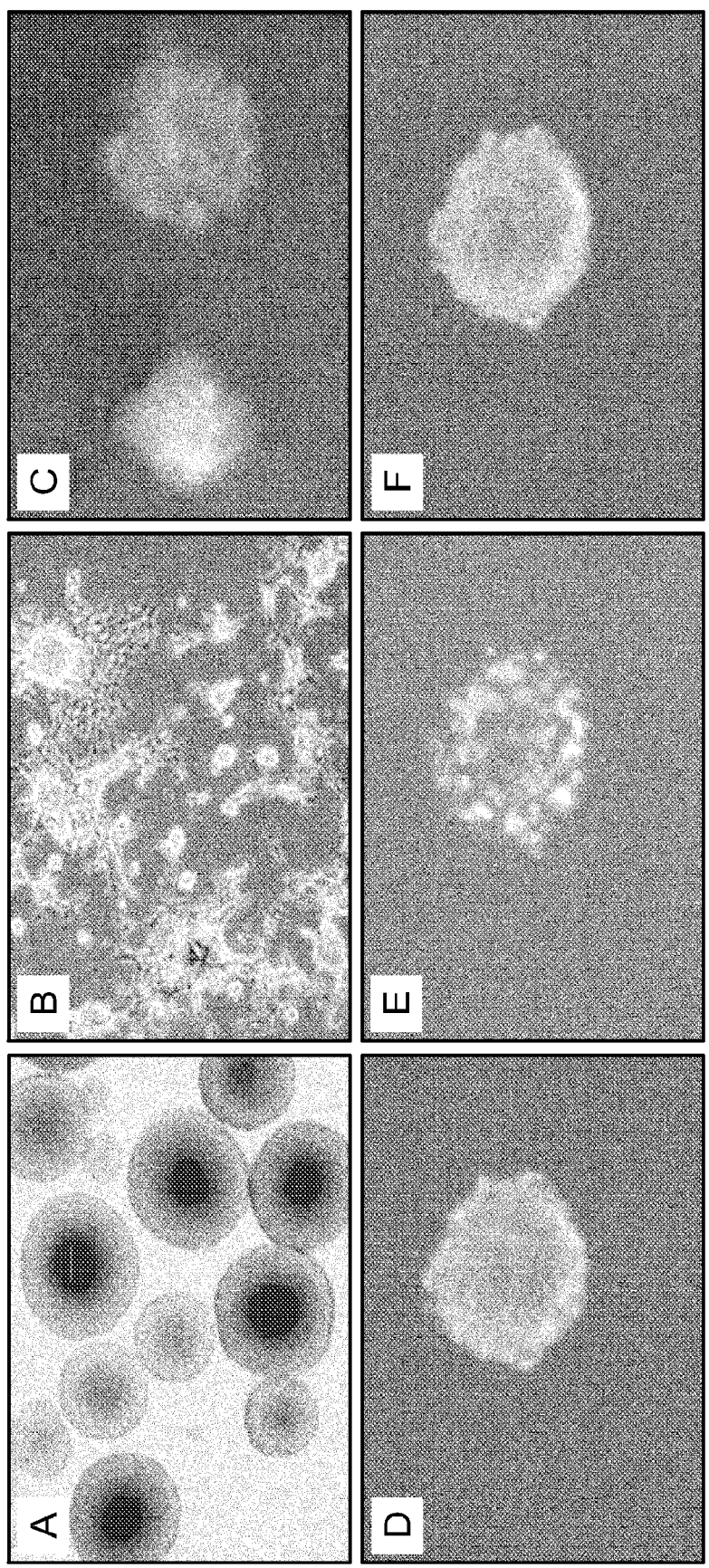
FIG. 2 shows NSCs obtained from the cerebellar cortex proliferate as neurospheres (A), express eGFP (C) and nestin (D-F), and differentiate in adherent culture in the absence of mitogens (B). E=Hoechst.
Figure 3:
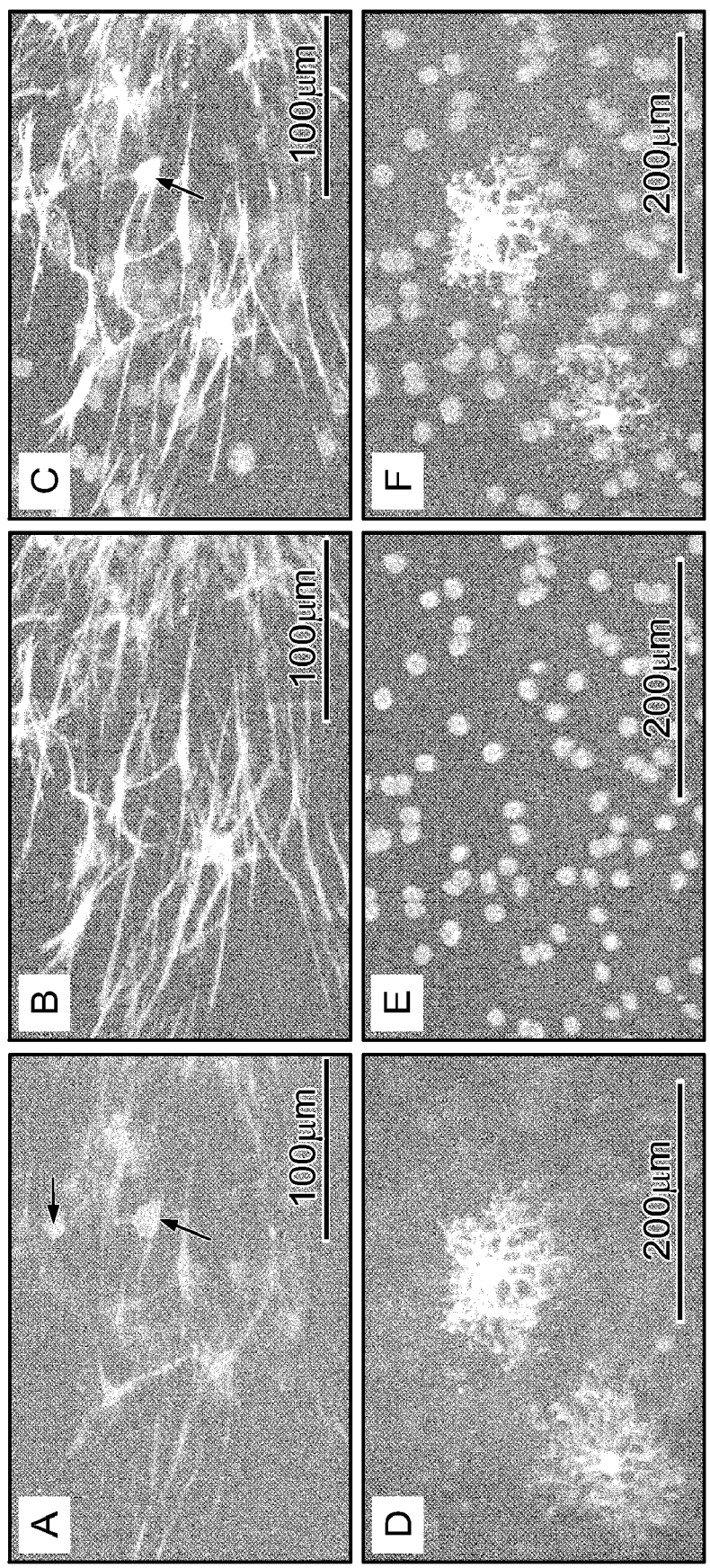
FIG. 3 demonstrates trilineage differentiation of cerebellum-derived NSCs into Tuj1+ neurons (A, arrows), GFAP+ astrocytes (B), and MBP+OL (D). C and F are overlays of AB and DE, respectively. E=Hoechst.
Figure 4:
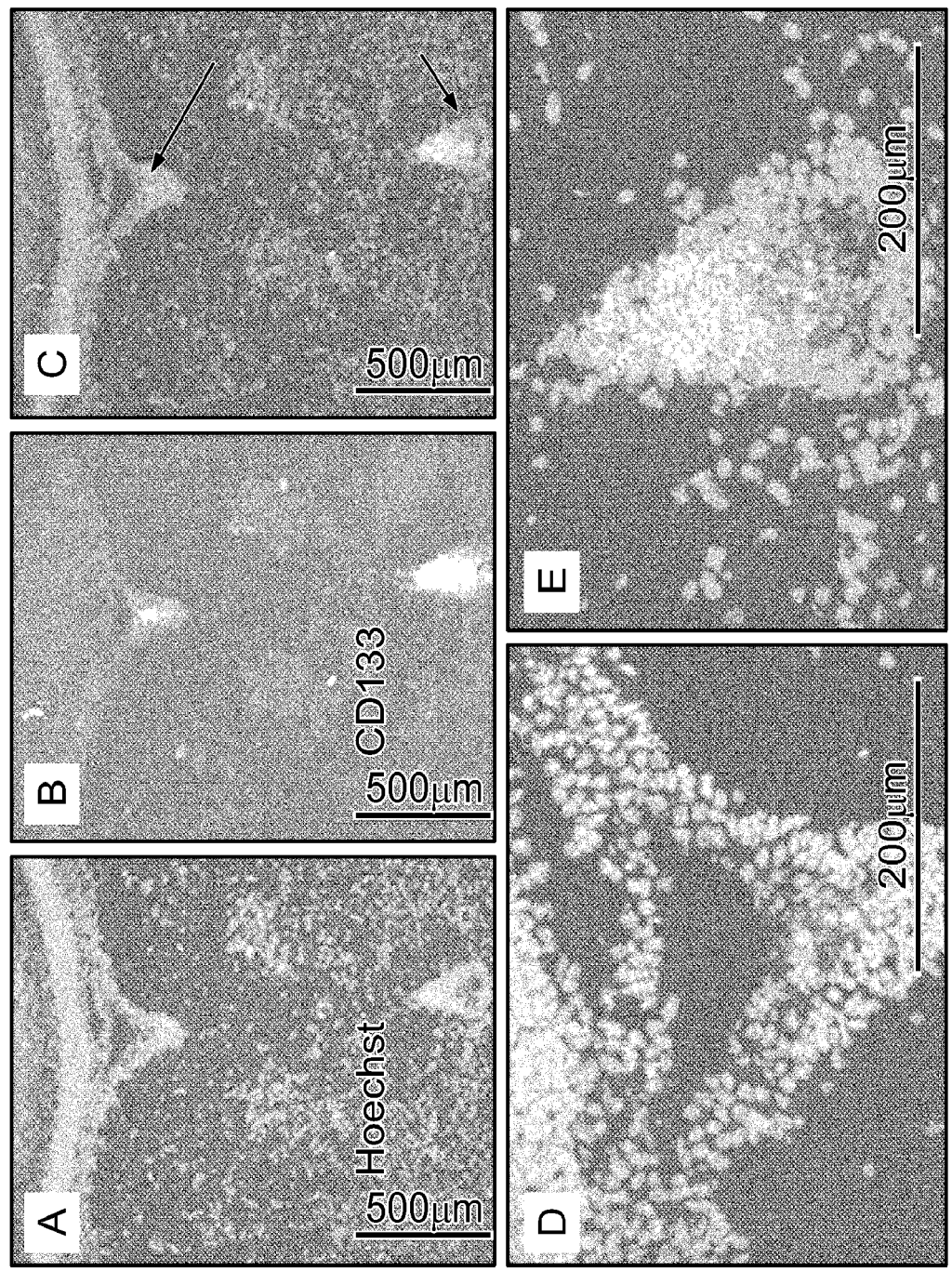
FIG. 4 shows a coronal section through the fourth ventricle, illustrating expression of CD133 in two clusters of cells in the ventricular wall. Arrow indicates the region shown at higher mag in (D), arrowhead indicates region in (E). These cells also express noggin, nestin, and β-gal.

A protocol was optimized to isolate, expand and differentiate cerebellum neural stem cells (CBNSC) from adult mice. Cerebella were dissected and white matter removed. Cells were dissociated, grown in suspension culture for 2 weeks in 6 well plates in media containing EGF and FGF2 forming neurospheres (FIG. 2A). Given the few data available regarding CBNSC culture, clonal experiments similar to those employed for subventricular zone (SVZ) neurospheres were initially carried out. Single spheres were dissociated and grown to obtain secondary, tertiary and quaternary spheres. From six independent clones, the spheres were passaged five times, consistent with the presence of a NSC. Clonal spheres expressed eGFP after in vitro induction (FIG. 2C) and nestin (FIGS. 2D-2F) and eGFP after in vitro induction (FIG. 2C). Differentiation assays (FIG. 2B) indicated that the cells are multipotent, forming GFAP+ astrocytes, Tuj1+ neurons and MBP+ oligodendrocytes (FIG. 3).

To enrich this population, cells were sorted based on the binding of the fluorogenic β-gal substrate, FDG (fluorescein di-(beta)-D-galactopyranoside; Hendricks et al., 1999, *Eur. J. Immunol.,* 29:1912-8) using FACS. Based on the expression of β-galactosidase under the nestin-II enhancer promoter region in nestin-rtTA mice, it was determined that the β-gal+ primitive NSCs make up 0.2-0.37% of the total population. Sorted cells divided in vitro, forming primary and secondary spheres that underwent trilineage differentiation.

Example 2

Characterization of Adult Cerebellum-Derived NSCs

The adult cerebellar cortex typically is free of any dividing cells. However, in the presence of noggin, cerebellar stem cells (CBSC) were induced to divide. No other growth factor or growth factor combination has been shown to promote proliferation within the cerebellar cortex. The cerebellum-derived adult NSCs described herein express Sox1, Sox3, Sox9, BLBP, and nestin. In vitro, these cells have the ability to self renew when grown in the presence of FGF2 and EGF and, in serum-containing medium, they undergo multilineage differentiation, forming neurons, astrocytes and oligodendrocytes.

Compared with control cultures, where 89.7±4.3 percent of the cells were GFAP+ astrocytes, cultures exposed to noggin formed only 81.3±2.6 GFAP+ astrocytes, p≤0.01. In control conditions 5.9±2.3 percent of the cells were neuronal as assessed by their expression of BIII tubulin (Tuj1 antibody), while noggin exposed cultures formed 12.5±2.6 neurons, p≤0.05. Finally, oligodendrocyte differentiation was also stimulated by noggin, from 1.5±0.8 to 6±1.8 percent of the cells, p≤0.01. When LIF was added to the control cultures, there was no stimulation of oligodendrocyte differentiation, but when added to the noggin cultures, there was a three-fold increase in oligodendrocytes.

Example 3

Microarray Analysis of Adult Cerebellum-Derived NSCs

To identify novel patterns of gene expression in cerebellum-derived neural stem cells (NSCs), cells microdissected from the adult cerebellar cortex were sorted based on the binding of the fluorogenic β-galactosidase substrate FDG (fluorescein di-(beta)-D-galactopyranoside). Since β-gal expression was restricted to the nestin+ cerebellum-derived NSCs of the cortex, the FDG+ group was composed solely of cerebellum-derived NSCs. It was determined that cerebellum-derived neural stem cells make up 0.2-0.37% of the total population, and their gene expression was compared with that of cerebellar cortical cells that did not express β-gal (and, therefore, nestin); a population including Purkinje, granule, basket and stellate neurons. The gene expression profile of cerebellum-derived neural stem cells was examined by hybridizing RNAs from sorted cerebellum-derived neural stem cells to Affymetrix mouse 430 2.0 arrays by the University of Michigan Cancer Center Microarray Core. Data were analyzed using Robust Multichip Averaging (RMA), and then probe sets with >2 fold changes relative to controls were selected for analysis. This initial analysis identified 269 genes that were up-regulated in the stem cell population, and 225 genes that were strongly down-regulated in this population as compared to control neurons. Functional annotation clustering identified 8 clusters of genes that were significantly differentially expressed, with annotations shown in Table 1.

TABLE 1

| Gene Categories from Microarray | |
|---|---|
| DNA repair | 27 |
| Nucleotide binding | 81 |
| Nucleoside binding | 72 |
| Differentiation | 20 |
| ATP-binding | 63 |
| DNA recombination and repair | 15 |
| Ras signaling | 9 |
| Positive regulation of macromolecule biosynthesis | 40 |

A number of genes including: Mbp, Mobp, Plp1 were associated with myelination. Genes associated with neurite outgrowth (Gprn2, Epha7), many molecules involved in cell-to-cell adhesion and matrix metalloproteinases, which are required for cell migration, were identified in addition to Hhip and Gli1, which are members of the hedgehog signaling pathway. Additional patterning factors Hoxd3, Dlx5, Fez1, Bex4 were also enriched in the assayed cell population. Another gene that was down-regulated in both stem cell populations was Sox6, which has been shown to interfere with oligodendrocyte differentiation (Stolt et al., *Dev Cell.* 11(5):697-709 (2006)). A number of candidate cell surface molecules were identified which should permit prospective identification of cerebellum-derived neural stem cells in situ.

Section B. Transgenic Mouse Expressing Noggin

Example 1

Experimental Strategy

Control of the proliferation and lineage differentiation of adult neural stem cells (NSC) appears to be determined largely by components of the extracellular milieu, which must be understood and specifically manipulated to expand and mobilize this population for cell replacement applications. To understand the role of BMP/noggin signaling in lineage choice by NSC in the intact nervous system, the goal was to develop a transgenic mouse that could be induced to express noggin in the NSC compartment. Existing mice that express the reverse tetracycline-controlled transactivator (rtTA) protein under the control of the nestin intron II enhancer/promoter were obtained.

The class VI intermediate filament protein nestin was chosen to drive gene expression because it is expressed throughout the neuroepithelium during early CNS development, and is down-regulated with differentiation of stem cells to mature neurons and glial cells, remaining in the ventricular zone, then adult hippocampal dentate gyms, radial glia and SVZ. In fact, neuroblasts (A), neural stem cells (B), and transit amplifying C cells all express nestin. Nestin expression is not restricted to the nervous system, and it has been shown that regulatory elements in intron I of the nestin gene control expression in other cell types, particularly myogenic cells, while CNS expression is controlled by elements in intron II.

To generate a transgenic mouse having an inducible noggin gene, mice as described below were used. These mice contain a β-geo element that confers both antibiotic resistance and β-gal expression to nestin+ neural stem cells (vector A). Hemizygous embryos express β-gal in the neuroepithelium (E10-17) followed by expression in adult neural stem cell populations (dentate gyms and subventricular zone). This strain has been employed widely to target inducible gene expression to the CNS during early developmental stages (pan-neuroepithelium) and to neural stem cells in the adult.

Figure 5:
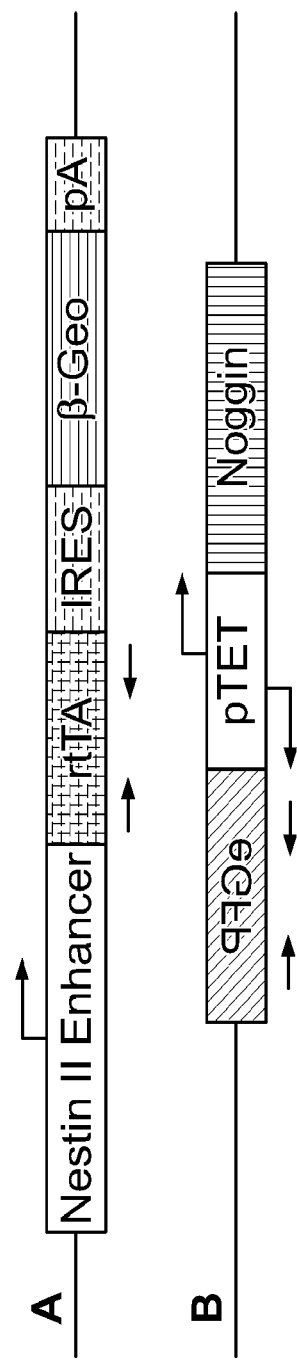
FIG. 5A shows a schematic of the plasmid used to construct the existing Nestin-rtTA mouse. The Nestin intron II enhancer/promoter region (white box) controls expression of the reverse transactivator (rtTA; yellow box); an internal ribosome entry site (IRES: light blue) drives expression of β-geo (β-galactosidase fused to neomycin phosphotransferase (dark blue).
FIG. 5B shows the new transgene: pBi-Noggin-eGFP contains a bidirectional tetracycline inducible promoter (pTET; white box) controlling expression of the enhanced green fluorescent protein (eGFP; green box) and noggin (red box). Black arrows indicate promoter directions and red arrows indicate the position of PCR primers employed for genotyping.

To generate double transgenic mice, the pBi-noggin-eGFP construct (FIG. 5B) was developed using the pBi vector (Clontech). In the presence of doxycycline (Dox), transcription of the target genes (noggin and eGFP) was induced in cells where rtTA was expressed (nestin expressing progenitors). Male mice were mated with superovulated FVB/N females in the Transgenic Core at the University of Michigan; fertilized eggs were injected with linearized pBi-noggin-eGFP DNA; and the eggs were transferred to pseudopregnant females. After five independent injections and transfer to 12 recipient females, 107 animals were obtained and analyzed for the presence of the transgenes.

Genomic DNA from tail biopsies was amplified using primers (red arrows in FIG. 5) to detect rtTA and eGFP. PCR conditions were optimized to be able to detect a single copy of the transgene in the presence of 2 μg of genomic DNA. Eleven different animals carrying the pBi-Noggin-eGFP transgene were identified, and were then mated with nestin-rtTA mice to obtain double transgenics. After breeding, double transgenic offspring were identified by PCR with specific primers for eGFP and rtTA.

Validation was carried out at a number of steps, including: genotype, faithful expression of β-gal and eGFP in nestin expression zones, overlap with endogenous noggin, and inducibility of the transgene. Based on these criteria, three lines of animals were selected to expand for detailed analysis.

Example 2

Fidelity of β-Gal Expression

Figure 6:
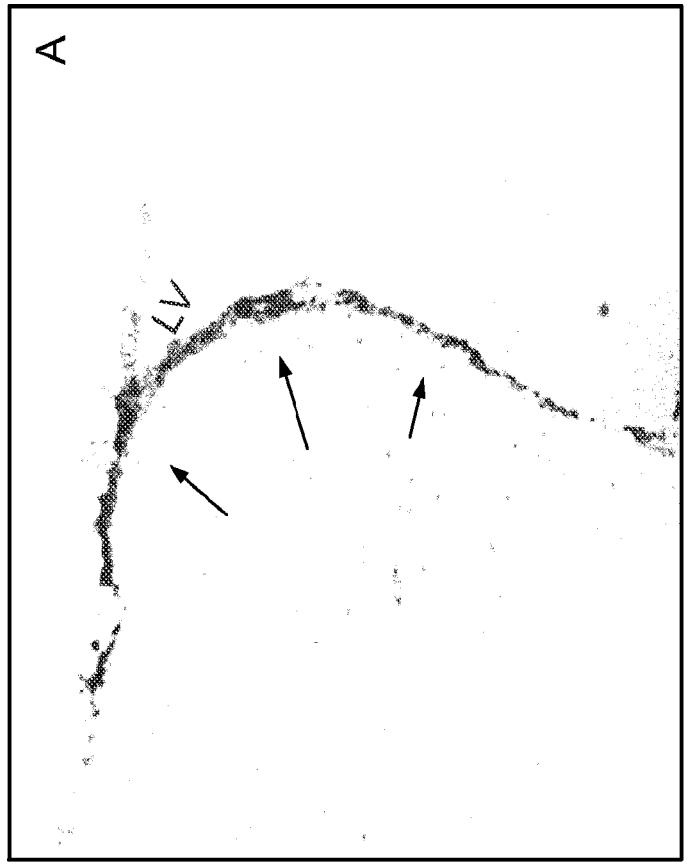
FIG. 6 shows coronal sections through the lateral ventricle (LV). β-gal was localized to the subventricular zone (SVZ) using X-gal staining (A) and nestin was detected using immunohistochemistry (B) to confirm an overlap in expression. Arrows indicate SVZ.
Figure 6:

The nestin enhancer reliably targets β-gal (and thus rtTA) to the population of cells that normally express nestin. Expression of the nestin-rtTA transgene was monitored using X-gal staining and immunohistochemical localization of nestin, with complete overlap observed. There was X-gal staining in the subventricular zone of the lateral ventricle (FIG. 6A), in the OB, hippocampus, in the Purkinje cell layer of the cerebellum, and in cells scattered throughout the cortex. This pattern was similar to that previously described for the nestin enhancer-eGFP construct. Strong β-gal expression was observed, but ectopic expression outside the nervous system was not detected.

Example 3

Inducibility of the Transgene

Double transgenic animals were initially studied to identify lines of mice in which doxycycline hydrochloride (Dox, 2 mg/mL; Sigma) exposure via the drinking water reliably induced noggin gene expression. 200 μg/mL Dox in drinking water has been shown to produce saturating steady state levels after 6 hours, and after Dox removal, serum was cleared with a half-life of 6 hours. The original description of the nestinrtTA animals reported that transgene expression was detectable after 6 hours of treatment with Dox, maximal induction was observed after 12 hours of treatment with Dox, and transgene expression returning to 2-fold after 12 hours of withdrawal, indicating that expression of the transgene can be rapidly induced by Dox exposure. Transgene expression level can also be controlled by increasing Dox levels. The transgene here was expressed throughout the CNS in proliferating progenitors, and was absent from skeletal muscle and visceral organs.

The controls used were double transgene carriers with normal drinking water; and nestin rtTA mice and wild type animals exposed to Dox. Founder lines were identified that exhibit varying levels of expression following induction. Three were particularly good and were studied in more detail.

Figure 7:
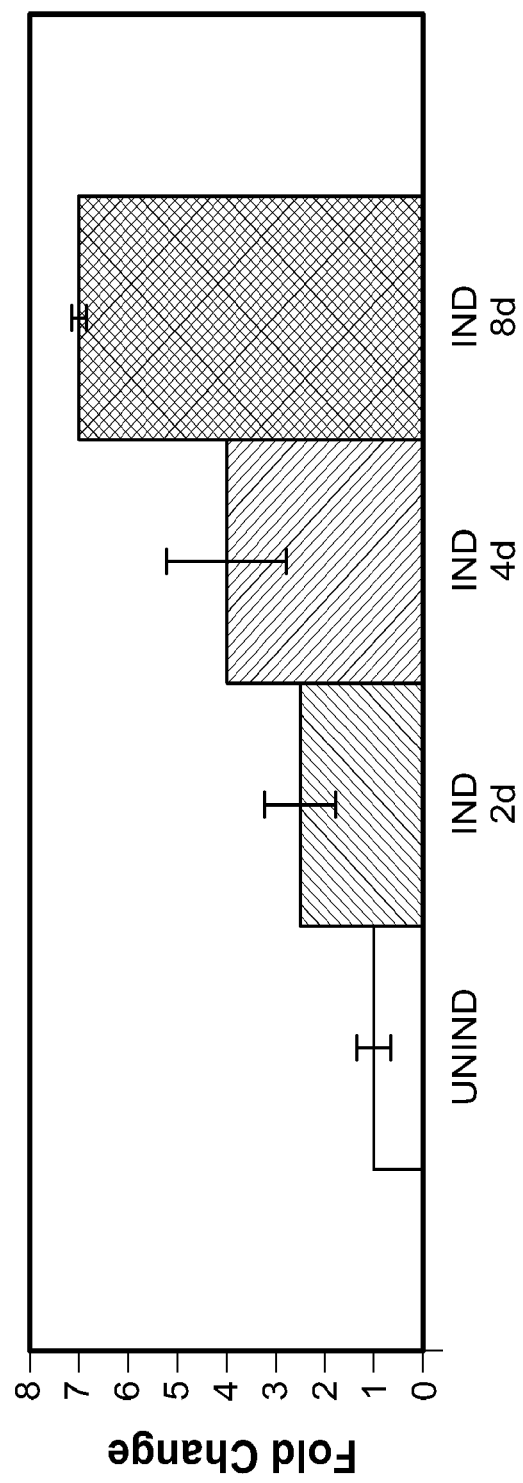
FIG. 7 shows the expression of noggin mRNA in SVZ that was microdissected from four control and four double transgenic mice exposed to 2 mg/ml of the tetracycline analog, doxycycline (Dox) in the drinking water for 2, 4, and 8 days. RNA was extracted using Trizol and subjected to Q-PCR analysis to examine noggin expression, which was increased 7-fold over controls after 8 days of induction.

Transgene inducibility was examined using Q-RT-PCR. There was a 2-fold up-regulation of noggin expression after 2 days of exposure to Dox, a 4-fold up-regulation after 4 days exposure to Dox, and seven-fold up-regulation after 8 days exposure to Dox in adult (8-10 week old) animals compared to the controls (FIG. 7).

Figure 8:
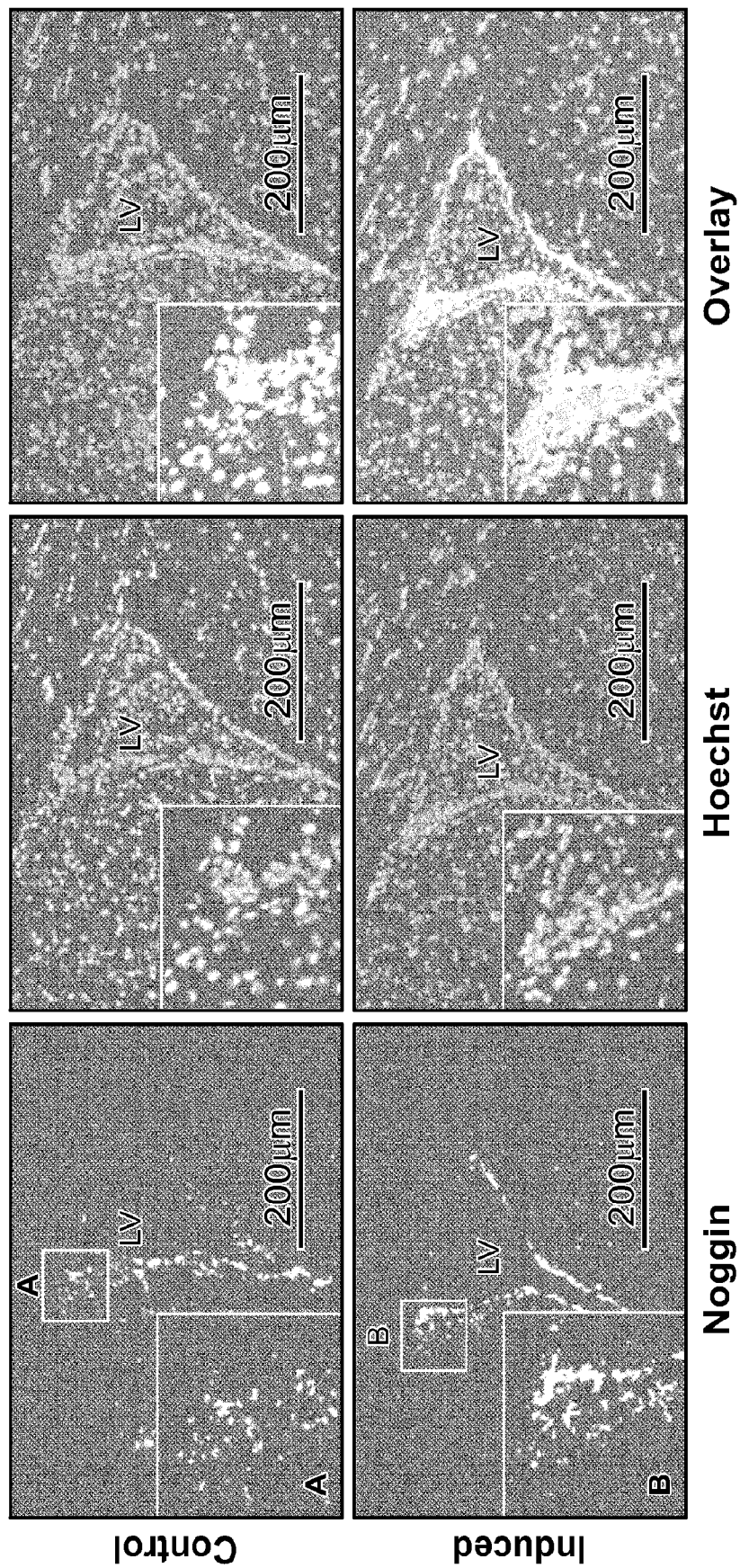
FIG. 8 shows coronal sections through the lateral ventricle (LV) of double transgenic mice. Control animals (top row, A) expressed noggin in the ependymal layer, while induced animals (bottom row, B) showed an increase in noggin expression throughout the SVZ.
Figure 9:
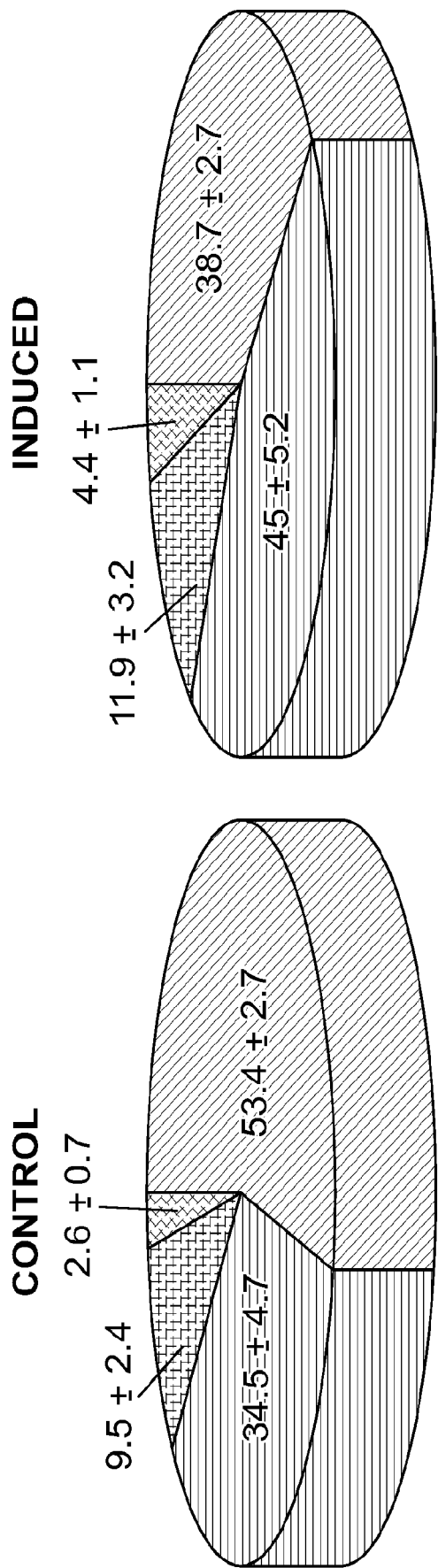
FIG. 9 is a graph showing that induction of noggin expression increases the number of transit amplifying C cells, neuroblasts (NB) and oligodendrocyte progenitor cells (OPC) in the SVZ at the expense of GFAP+ cells.

Noggin expression was also examined using immunohistochemistry with an anti-noggin antibody (Santa Cruz) to identify both endogenous and transgene-driven expression. In the adult SVZ, noggin was expressed by ependymal cells (FIG. 8A); expression increased following 8 days of exposure to Dox (FIG. 8B). Transgene driven expression of noggin was observed in the SVZ, hippocampus, cerebellum, OB, and in scattered cells in the cortex.

Example 4

Effects of Transgene Expression

A. The In Vivo Effects of Noggin Expression on Differentiation 8-10 week old mice from three founder lines were treated with Dox for eight days, and then their brains were removed, sectioned and immunohistochemical localization of cell type restricted proteins was performed (FIGS. 9-13). The following proteins were used (with the cell-type they're associated with indicated): doublecortin (DCX; neuroblasts), GFAP (astrocytes), Olig2 (oligodendrocyte progenitors; OPC), Mash1 (transit amplifying C cells), Tuj1 (maturing neurons) or NeuN (maturing neurons). To avoid regional heterogeneity, analysis was focused on a discrete region of the SVZ (0.26-0.98 from Bregma) in four sections per animal, with 5 animals per group. Data were analyzed using two-tailed t-tests in SPSS, and are expressed as mean percentage ±SD.

Figure 10:
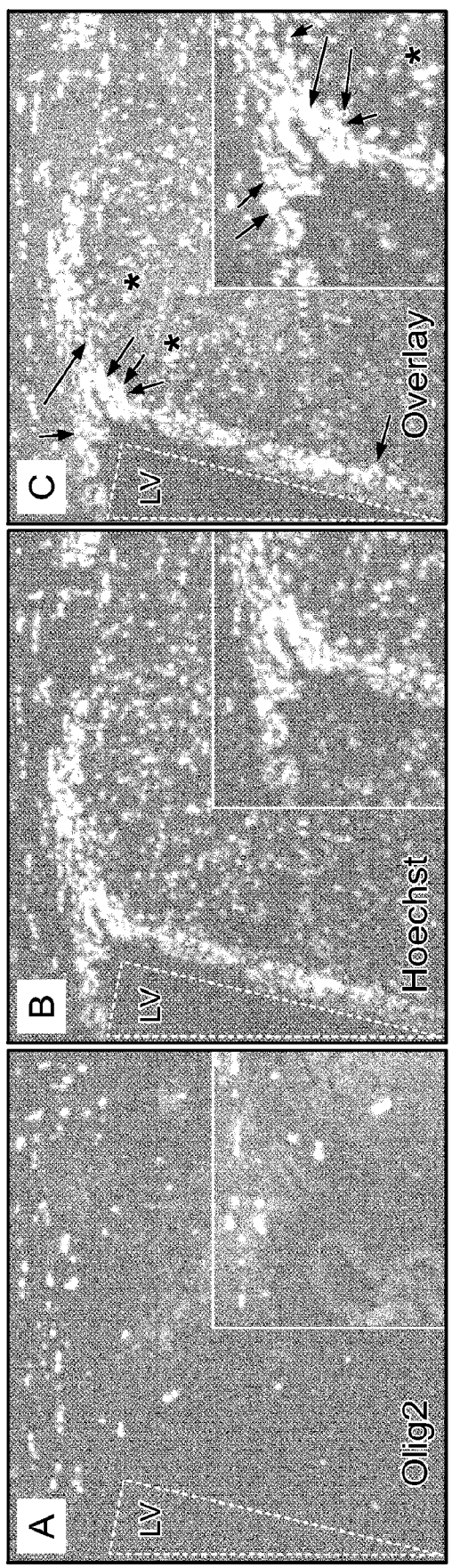
FIG. 10 shows that the number of Olig2+ cells (arrows) was significantly increased following induction of noggin expression. OPC in the striatum (*) were not included in the analysis.
Figure 11:
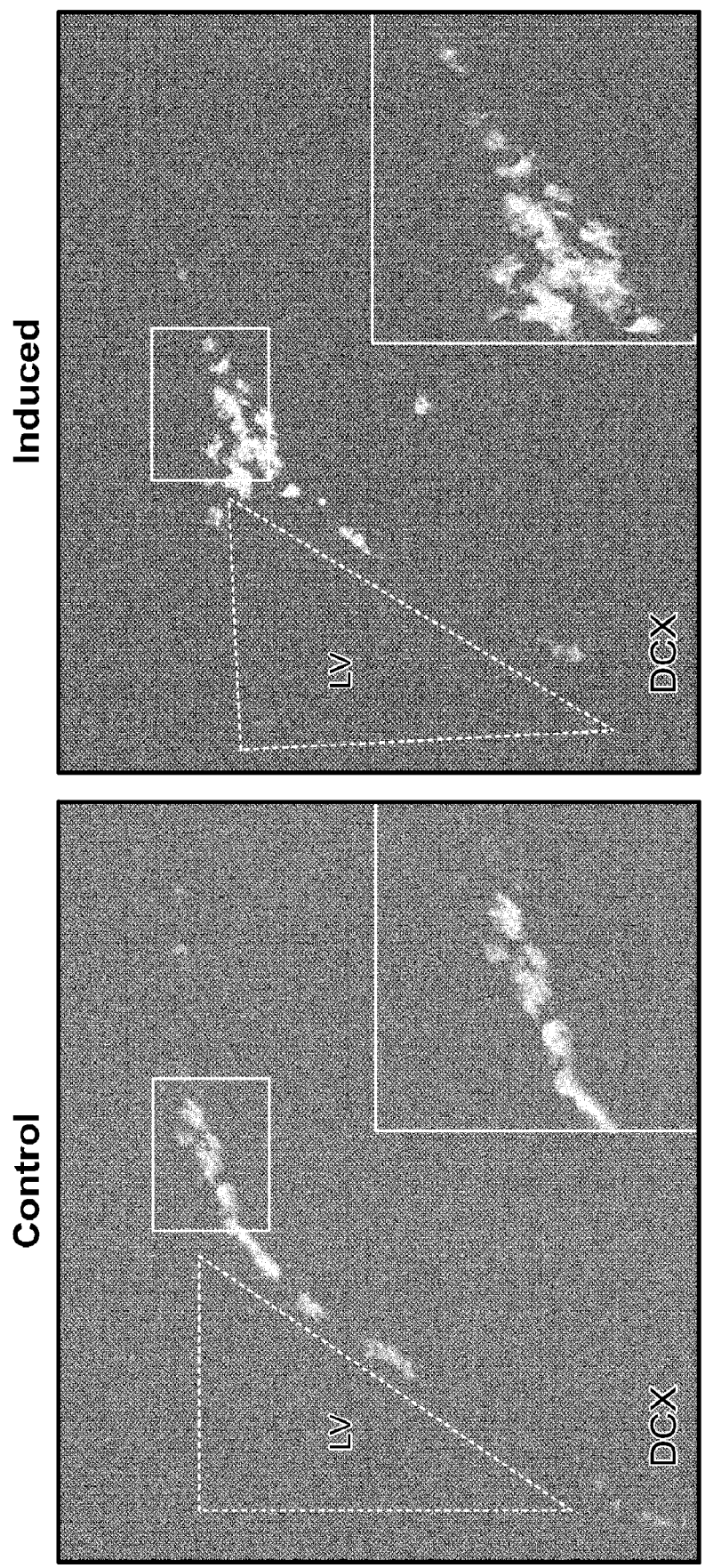
FIG. 11 shows that the induction of noggin expression by 8-day exposure to Dox significantly increased the number of neuroblasts (DCX+ cells) present in the SVZ. These data indicate that noggin expression enhances neurogenesis by increasing the number of NB present in the SVZ.
Figure 12:
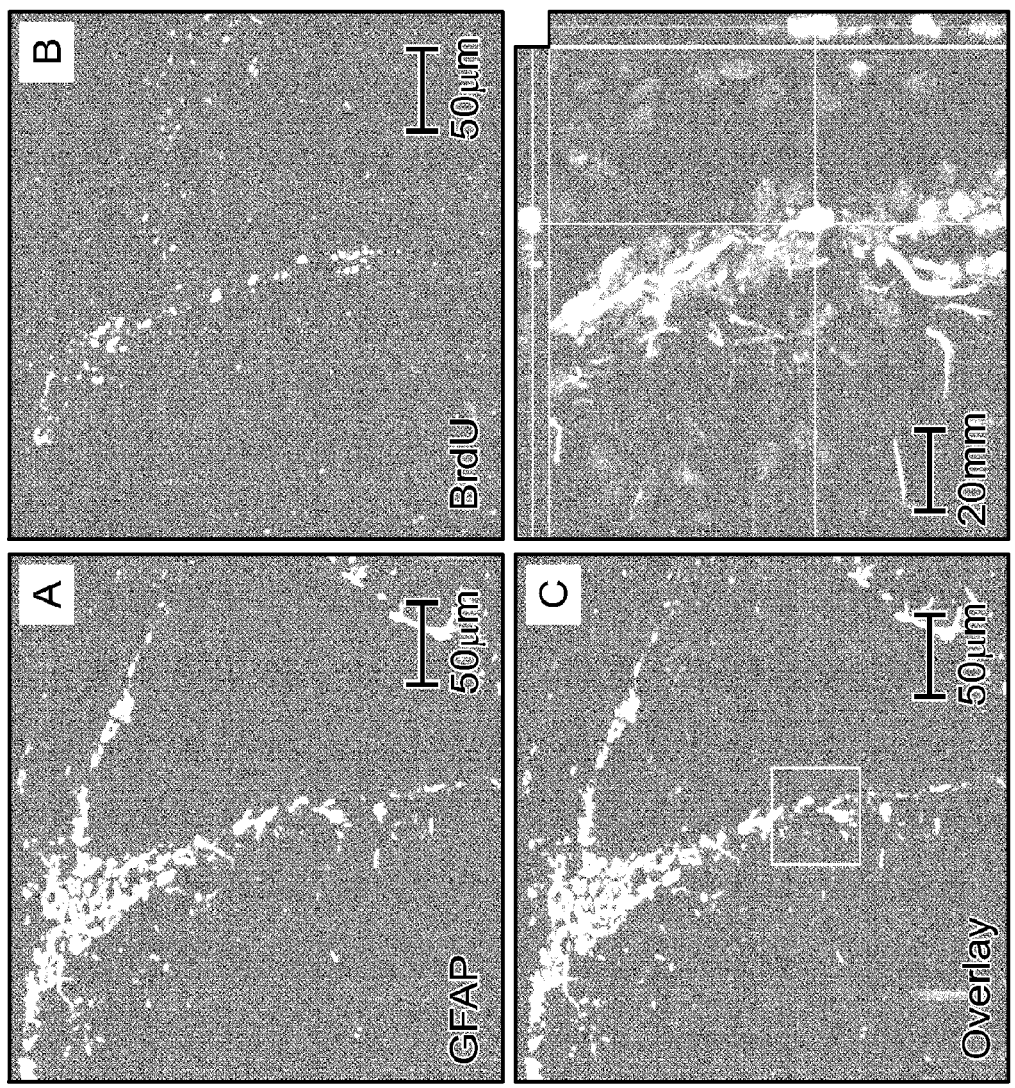
FIG. 12 shows a confocal microscope view of a section of the LV from an 8-day Dox induced animal illustrating the expression of GFAP (A), BrdU (B), in overlay (C), and with dual channel localization (D). Confocal microscopy indicated that the BrdU+ nucleus is central to GFAP+ cytoplasm.

Noggin expression significantly expanded the DCX+ neuroblast pool (45±5.2 vs. 34.5±4.7, $p<7.9\times10^{-9}$; FIG. 11), Mash1+ cells (11.9±3.2 vs. 9.5±2.4, p<0.0008) and Olig2+ cells (4.4±1.1 vs. 2.6±0.7, $p<8.2\times10^{-5}$; FIG. 10) in the SVZ. There were significantly fewer GFAP+ cells (38.7+2.7 vs. 53.4+2.7, p<0.0002; FIG. 12). Since there was no difference in the expression of activated caspase-3 between groups, and there was little overall cell death, it appears that the reduced number of GFAP+ cells is due to an alteration in lineage differentiation, with noggin favoring production of transit amplifying C cells, neuroblasts (A) cells and oligodendrocyte precursor cells (OPCs) at the expense of GFAP+ cells. The initial detailed analysis focused on the SVZ, but similar data has been acquired for other regions. Preliminary analysis of the subgranular zone (SGZ) of the hippocampus indicates that noggin stimulated proliferation (1.07±0.2 vs. 0.76±0.2) and neurogenesis (30.4±1.6 vs. 27.6±1.4) in this region as well.

These results indicate that, in vivo, noggin expression expands the population of neuroblasts, transit amplifying C cells, and OPCs at the expense of GFAP+ cells in the SVZ.

B. The In Vivo Effects of Noggin Expression on Progenitor Proliferation

Additional adult (8-10 week) double transgenic mice were exposed to Dox for eight days and given a single injection of bromodeoxyuridine (BrdU; 100 mg/kg) on day 4 of induction. At the end of eight days, brains were sectioned and immunohistochemical localization of BrdU and cell type specific antibodies was carried out to monitor the progress and phenotype of recently divided cells. Noggin induction significantly increased the overall number of BrdU+ cells in the SVZ, the mean number of BrdU+/GFAP+ cells from 4.1±1.3 to 5.9±1.8; p<0.0001 (FIG. 12), and increased the mean number of DCX+/BrdU+ neuroblasts from 10.9±3.9 to 14.9±4.2; p<0.0007. Proliferation of Mash1+ cells was assessed using Ki67. Noggin increased C cell proliferation to 40.9%±6.8 compared with 29.1%±6.5 in uninduced controls; $p<1.2\times10^{-5}$. Data were confirmed in two independent experiments using two double transgenic lines. These data indicate that, in vivo, noggin expands the B cell pool and regulates progenitor proliferation of A, B, and C cells in the SVZ.

Figure 13:
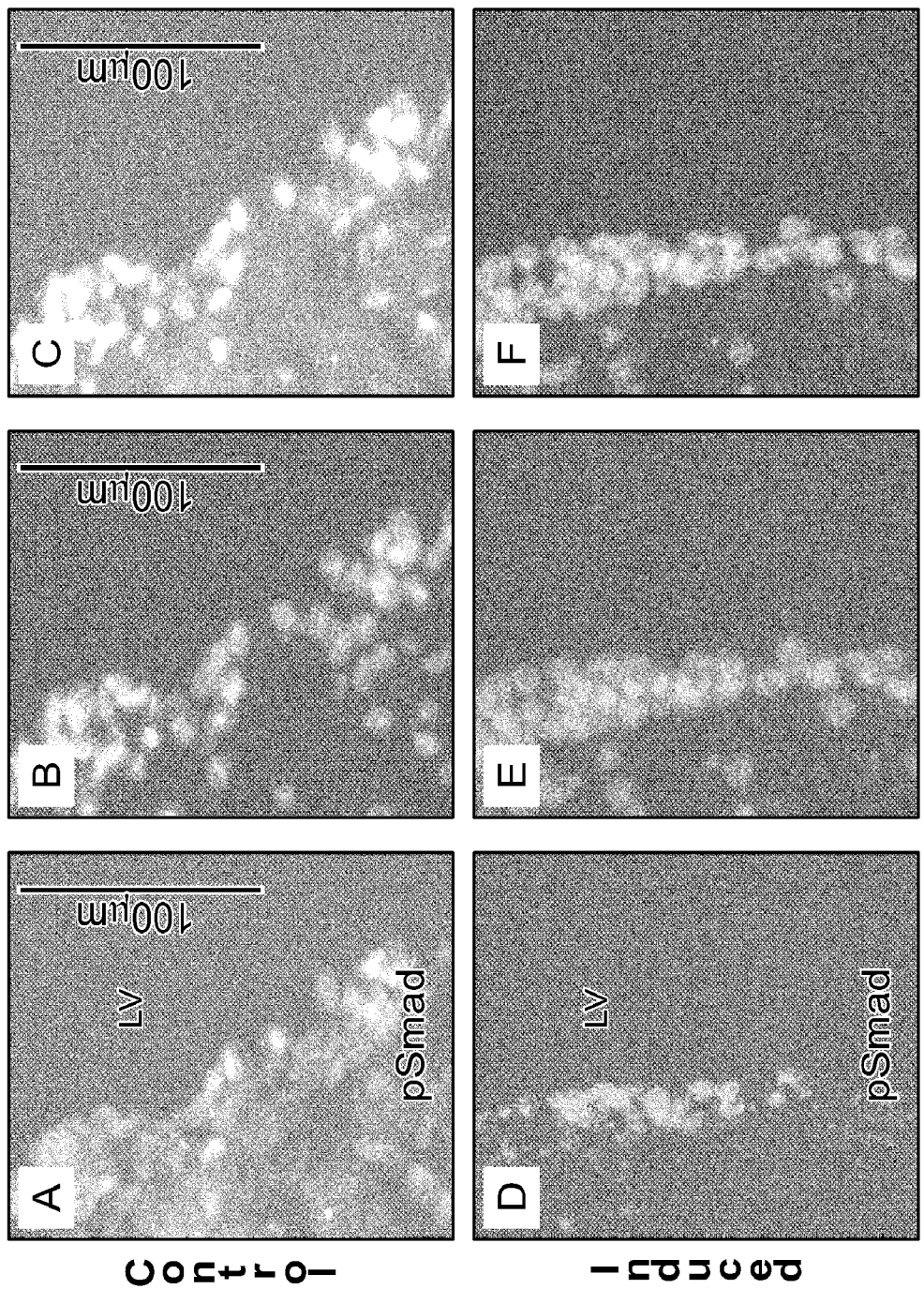
FIG. 13 shows coronal sections through the lateral ventricles of control (A-C) and double transgenic mice induced to express noggin for 8 days (D-F). pSmad1/5/8 localization in the uninduced control is strongly nuclear (A), overlapping with the Hoechst nuclear stain (B), unlike the cytoplasmic localization of the staining in induced animals (D-F).
Figure 14:
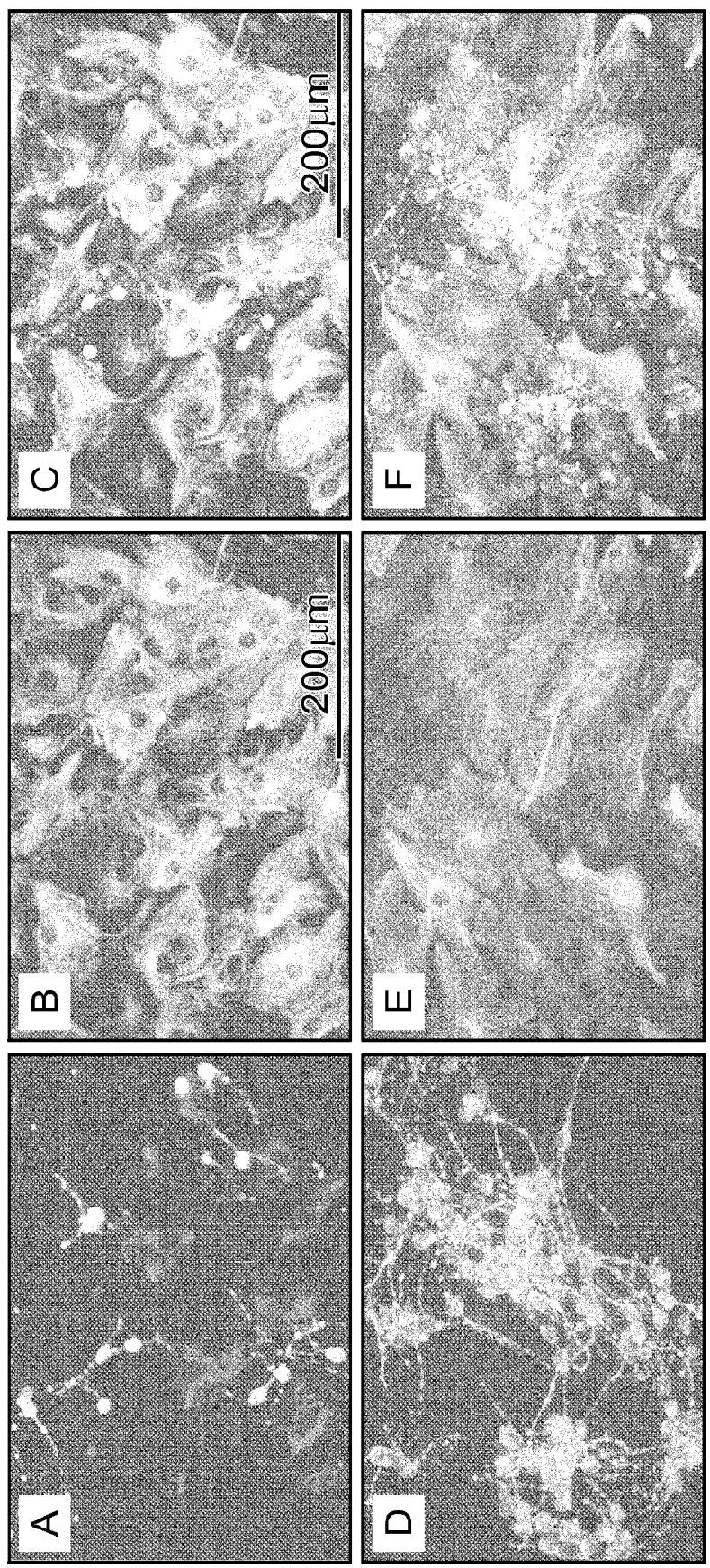
FIG. 14 shows that, after 7 days of in vitro differentiation, there were significantly fewer neurons (Tuj1+ cells) in controls (A-C) compared with cultured neural stem cells derived from animals induced 8 days in vivo (IND; D-F), while the number of astrocytes (GFAP+) was decreased in the induced cultures (D-F).
Figure 15:
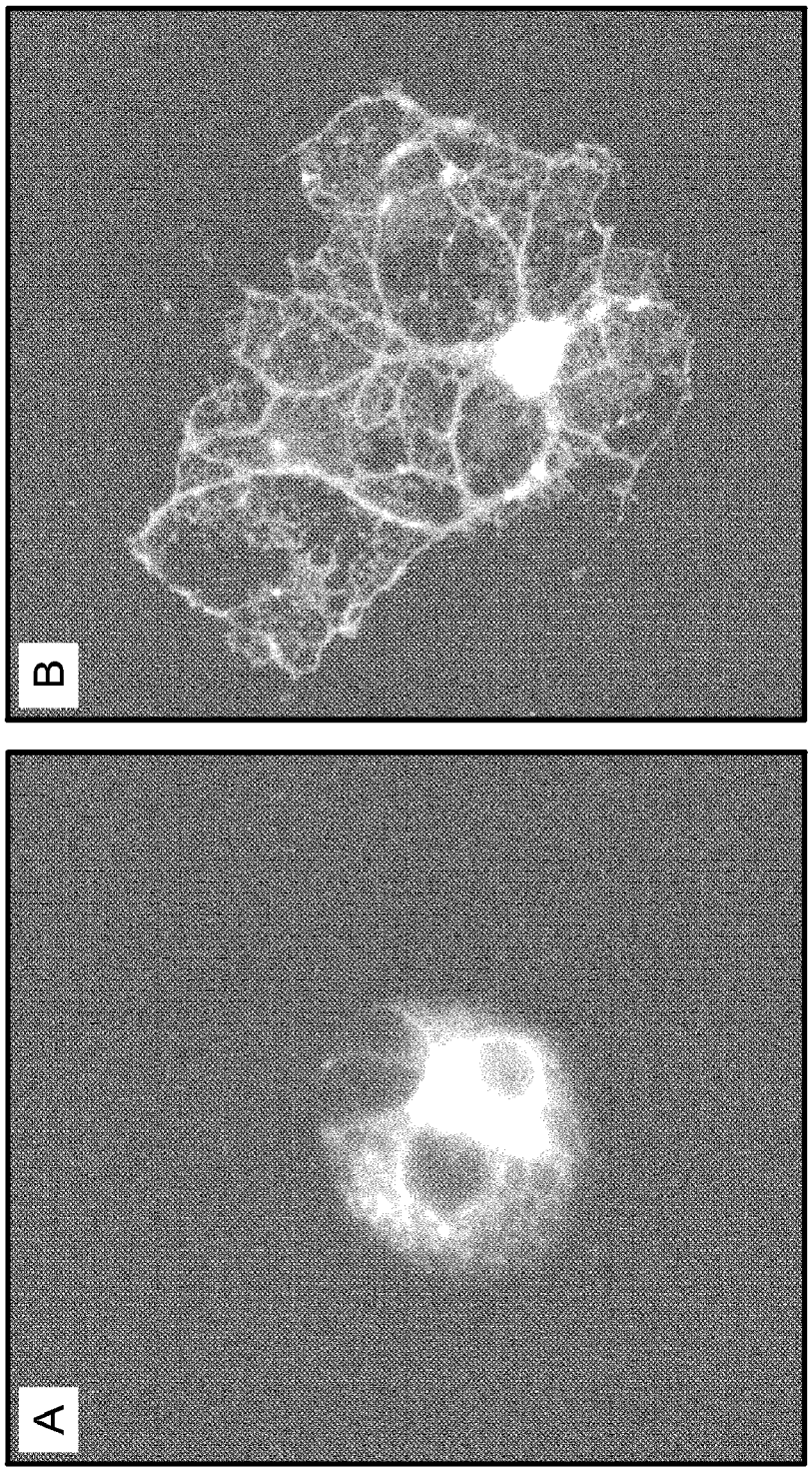
FIG. 15 shows that, compared with MBP+ oligodendrocytes in control cultures (A), noggin increased both the number and maturity of OL (B).

To determine if noggin interferes with BMP signal transduction, an antibody that identifies phosphorylated Smad1, Smad 5, and Smad8 (referred to herein as "Smad1/5/8") was employed. Smad1/5/8 transduces activated BMPR signals to the nucleus. In uninduced animals, phospho-Smad1/5/8 was present in the nuclei, indicating active BMP signaling, unlike noggin-induced animals, where phospho-Smad1/5/8 expression was attenuated (FIG. 13).

Example 5

Microarray Analysis of SVZ Neural Stem Cells

Microarray analysis of RNAs from microdissected SVZs from adult double transgenic animals induced for 8 days with Dox (n=4, pooled) compared with RNA from uninduced control mice (n=4) was carried out (at the University of Michigan arraying core in the Comprehensive Cancer Center) to identify any unexpected effects of noggin expression. RNAs were hybridized to Affymetrix mouse 430 2.0 arrays. Data were analyzed using RMA, and probe sets with >2 fold differences, with the added criterion that at least one sample had an expression level of $2^6$ or higher, were selected for analysis. This methodology identified 436 differentially-expressed probe sets; of which 206 were up-regulated in the noggin group and corresponded to gene ontology classifications indicated in Table 2.

Genes associated with NSC, neurons and oligodendrocytes (OL) were upregulated. Prominin1, Hes5, and EGFr were strongly up regulated. OL-associated genes that were up-regulated included: Mag, Mog, MBP, PMP22, Ugt8a, CNP and Sox8. Interestingly, the D class Sox family member Sox 6, which specifically interferes with Sox8 mediated oligodendrocyte differentiation, was down-regulated in the noggin population. Neuronal markers including: FoxP1 (forebrain (Takahashi 2008), medium spiny striatal neurons (Arlotta et al., 2008, *J Neurosci.* 28(3):622-32), Fezf2 (involved in establishing neuronal identity (Molyneaux et al., 2007, *Novartis Found Symp.* 288:3-15) and differentiation of projection neurons from the SVZ (Chen et al., 2008, *Proc Natl Acad Sci USA.* 105(32):11382-7), the atonal-related BhlhbS TF (aka Bhlhe22) involved in neocortical neurogenesis (Joshi et al., 2008, *Neuron* 60(2):258-72) and Zhx1 (Barthelemy et al., 1996, *Biochem Biophys Res Commun.* 224(3):870-6) were up-regulated. A novel cadherin, Cdh9, which was previously identified in oocytes (UniGene) and involved in neuronal migration in the PNS, and Zeb2 which is a transcriptional co-repressor of Ed-cadherin and Smad target genes (Sztriha et al., 2003, *Neuropediatrics* 34(6):322-5) were also increased in the noggin exposed population. The following genes were also up-regulated, but did not meet the expression level cut off: Olig1, Tenascin C, Neurod2, Neurod6, Nrg3, Pax6, β-III Tubulin, Sox2, and DCX. While such preliminary data must be verified by QRT-PCR, the observed expression patterns are consistent with data indicating that noggin expression promotes neuronal and oligodendroglia lineage differentiation, without inducing immune cytokines, damage- or apoptosis-associated genes.

TABLE 2

Gene Ontology Categories from Microarray

| | |
|---|---|
| Membrane | 49 |
| Unknown | 36 |
| Cytoskeleton | 29 |
| Transcription factors | 28 |
| Metabolism | 21 |
| Extracellular matrix | 14 |
| Cell cycle | 12 |
| Signaling | 10 |
| Cell growth/differentiation | 7 |
| RNA | 3 |

Section C. In Vitro Analysis of Noggin and LIF Compositions

Example 1

In Vitro Differentiation

Neurosphere assays were employed to determine the self-renewal and differentiation capability of putative NSCs. Somewhat surprisingly, noggin did not affect the self-renewal capacity of NSCs, consistent with the behavior of neurospheres derived from posterior SVZ, as 8-day noggin induction in 8-10 week-old double transgenic animals, followed by in vitro culture, had no effect on the size, proliferation or number of secondary neurospheres. Following mitogen withdrawal and plating on adhesive plastic substrates, however, noggin significantly increased the percentage of neurons (from 30 to 39%; $p<7.1\times10^{-7}$), and OL (from $4.8\pm2.8$ to $16.8\pm1.1$, $p<1.09\times10^{-5}$) and decreased the percentage of GFAP positive cells (from 68 to 60.5%, $p<6.5\times10^{-7}$) in these cultures.

When in vivo induction was followed by addition of Dox to the cultures (in vitro induction) (IND+DOX), the number of astrocytes was further decreased to 55% (UN vs. IND+DOX, $p<2.06\times10^{-8}$), the number of neurons increased to 45% (UN vs. IND+DOX, $p<1.5\times10^{-7}$), and the number of oligodendrocytes increased to $19.5\pm3.1$ (UN vs. IND+DOX, $p<4.1\times10^{-6}$). These data were obtained in five replicate experiments. Addition of BMP4 to the cultures significantly inhibited the effects of noggin expression on neuronal and OPC differentiation (+BMP4), confirming specificity.

To exclude effects of the culture paradigm per se, clonal analyses were also carried out. Cells were plated at 10 cell/well in 48 well plates, clones were expanded to secondary spheres, which were dissociated and grown to tertiary spheres, with five independent clones per group. There was no significant difference in the percentage of astrocytes, neurons or oligodendrocytes within groups, indicating that the results described herein are the effect of noggin expression and are not due to selective expansion of a progenitor cell or cells.

Neurospheres derived from double transgenic animals were induced in vitro to express noggin. Induction resulted in increased numbers of neurons and OL at the expense of GFAP+ cells. There was no difference in their self-renewal capability. These results demonstrate that the transgene can be induced in vitro.

Example 2

Induction with LIF

Human recombinant LIF was added to NSC differentiation cultures at 5 ng/mL at the time of plating. After 3 days in culture, media was partially replaced (half of the media was removed and the same volume of fresh media with LIF was added). Cells were grown at 37° C. and 5% $CO_2$ for a total of 7 days and fixed in 2% paraformaldehyde for 15 minutes at room temperature for immnunohistochemistry. To determine percentage of the three main neural cell types (neurons, astrocytes and oligodendrocytes), lineage specific markers were employed as follow: Tuj1, Neu N for neurons, GFAP for astrocytes and MBP for mature oligodendrocytes. Noggin stimulated the number of Tuj1+ neurons present in the cultures, and, when combined with LIF, increased the number of OL in the cultures by 2×.

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A method of inducing stem cells to differentiate into oligodendrocytes in culture, comprising:
   contacting stem cells in culture with a composition comprising a noggin polypeptide and a LIF polypeptide; and
   determining the percentage of oligodendrocytes in the culture.

2. The method of claim 1, wherein said stem cells are neural stem cells or embryonic stem cells.

3. The method of claim 1, wherein said noggin polypeptide is a mouse or a human noggin polypeptide.

4. The method of claim 1, wherein said LIF polypeptide is a mouse or a human LIF polypeptide.

* * * * *